US006999812B2

(12) United States Patent
Kawada et al.

(10) Patent No.: US 6,999,812 B2
(45) Date of Patent: Feb. 14, 2006

(54) ARTERIOSCLEROSIS DETECTION SYSTEM

(75) Inventors: Reiji Kawada, 5059, Kugacho, Kuga-gun, Yamaguchi 724-0300 (JP); Syoichi Takano, Saitama (JP)

(73) Assignees: BML, Inc., Tokyo (JP); Reiji Kawada, Yamaguchi (JP)

( * ) Notice: Subject to any disclaimer, the term of this patent is extended or adjusted under 35 U.S.C. 154(b) by 395 days.

(21) Appl. No.: 10/137,283

(22) Filed: May 3, 2002

(65) Prior Publication Data
US 2003/0009107 A1  Jan. 9, 2003

Related U.S. Application Data

(63) Continuation-in-part of application No. 10/111,101, filed as application No. PCT/JP00/07273 on Oct. 19, 2000.

(30) Foreign Application Priority Data
Oct. 22, 1999  (JP) .................................. 11-301565
Apr. 9, 2000   (JP) .............................. 2002-106211

(51) Int. Cl.
 A61B 5/02   (2006.01)
 A61B 5/04   (2006.01)
 G06K 9/00   (2006.01)
(52) U.S. Cl. ...................... 600/479; 600/480; 600/481; 600/504; 600/516; 382/128
(58) Field of Classification Search .............. 600/407, 600/434, 504, 561, 483, 457, 476, 480, 481, 600/482, 485, 479; 382/128; 351/221; 333/157
See application file for complete search history.

(56) References Cited

U.S. PATENT DOCUMENTS

| | | | | |
|---|---|---|---|---|
| 3,948,248 A | * | 4/1976 | Zuckerman et al. | ......... 600/457 |
| 4,572,199 A | * | 2/1986 | LaCourse | ................... 600/434 |
| 5,031,632 A | * | 7/1991 | Watanabe | ................... 600/504 |
| 5,116,116 A | * | 5/1992 | Aizu et al. | ................... 351/221 |
| 5,400,091 A | * | 3/1995 | Okazaki | ..................... 600/483 |
| 5,663,694 A | * | 9/1997 | Goebel et al. | ............... 333/157 |
| 5,847,806 A | * | 12/1998 | Mihashi | ..................... 351/221 |
| 5,976,096 A | * | 11/1999 | Shimizu et al. | ............. 600/504 |
| 6,390,989 B1 | * | 5/2002 | Denninghoff | ............... 600/561 |
| 6,621,917 B1 | * | 9/2003 | Vilser | ......................... 382/128 |
| 2002/0058874 A1 | * | 5/2002 | Ono et al. | ................... 600/476 |

* cited by examiner

Primary Examiner—Ali Imam
Assistant Examiner—Baisakhi Roy
(74) Attorney, Agent, or Firm—Sughrue Mion, PLLC

(57) ABSTRACT

An arteriosclerosis detection system including an electrocardiographic signal detection device, an eyeground image detection device for detecting an eyeground image in synchronization with an electrocardiographic signal detected by the detection device. The arteriosclerosis detection system further includes an eyeground vein constriction detection device for detecting the constriction of an eyeground vein in the vicinity of a site at which the eyeground vein and an eyeground artery cross each other. The constriction is detected based on the detected eyeground image in synchronization with the electrocardiographic signal. The arteriosclerosis detection system detects the eyeground image by executing an algorithm of software, which provides an eyeground image synchronized with an electrocardiographic signal by obtaining a stationary eyeground image synchronized with an arbitrary electrocardiographic signal from an animated eyeground image.

16 Claims, 17 Drawing Sheets

FIG. 6K
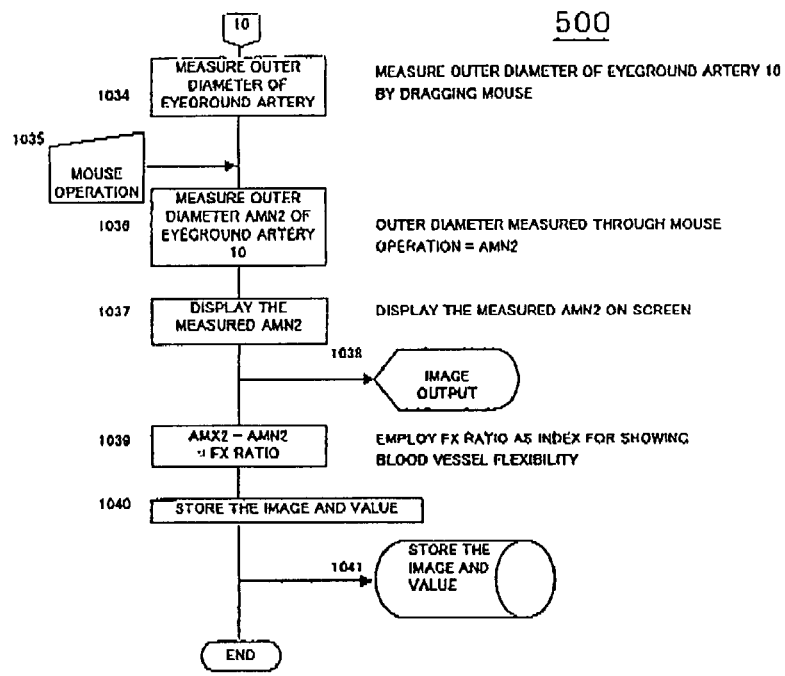
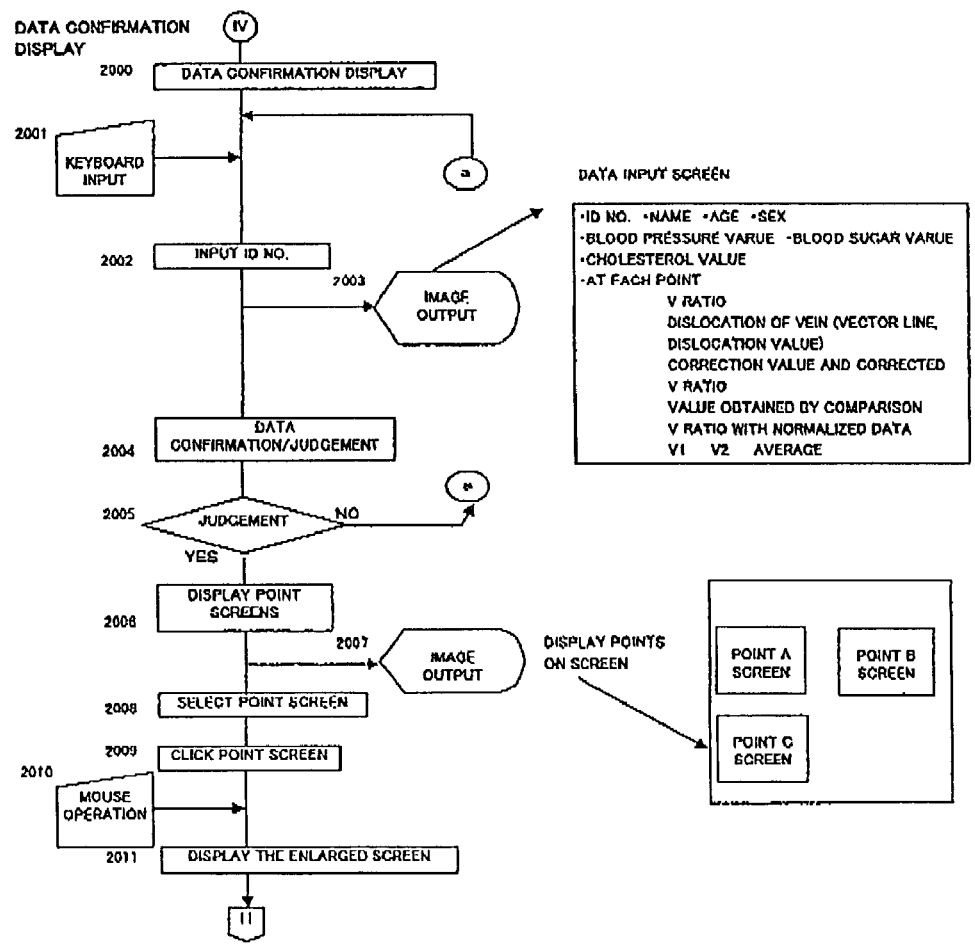

ARTERIOSCLEROSIS DETECTION SYSTEM

This application is a Continuation-In-Part application of parent U.S. patent application Ser. No. 10/111,101, filed May 22, 2003 corresponding to international application PCT/JP00/07273 filed Oct. 19, 2000.

TECHNICAL FIELD

The present invention relates to an arteriosclerosis detection system and to a method of using the system.

BACKGROUND OF THE INVENTION

In many countries faced with an aging population, care of the elderly has become an important issue. The greater the number of bedridden elderly people in a society, not only the heavier burdens imposed on the elderly themselves and their families, but also in increased social cost. Therefore, movements to ensure QOL (quality of life) of the elderly and to encourage self-support by the elderly have become more prevalent.

Promoting self-support of the elderly requires, in addition to their strong desire to stand on their own, prophylactic medical approaches for preventing onset of various diseases. Cardio-vascular diseases are commonly found among the elderly and frequently lead to bedridden lives, and pose serious problems to the aging population along with cancer. Arteriosclerosis, one of the major cause of cardio-vascular disease in geriatrics, often lead to ischemic heart disease, such as angina pectoris and myocardial infarct, and cerebral apoplexy such as cerebral infarction, cerebral hemorrhage or subarachnoidal hemorrhage.

With aging, certain degree of arteriosclerosis is developed in all. However, progress of arteriosclerosis may be retarded to some extent. That is, fatal damage to the arteries can be prevented by educational intervention concerning diet, exercise, and non-smoking as well as drug therapy and surgical intervention depending of the case.

However, in reality, convenient and precise diagnosis of artery conditions is not easy. At present, angiography is considered the best method for determining the condition of the artery. Since angiography is an invasive technique for the subject, method of diagnosis can only be applied to patients in serious condition of cardiovascular disease. Therefore, angiography cannot be employed primary screening method for detection of arteriosclerosis in asymptomatic patiens.

As an alternative to angiography, photographing of the eyeground; i.e., diagnosis on the basis of a photograph of the eyeground (hereinafter referred to as "eyeground-based diagnosis"), is employed as means for determining the conditions of arteries, particularly the cerebral arteries. Photographing of the eyeground is non-invasive to a subject, and can be performed conveniently. Therefore, this technique can be widely used in health monitoring checks and other types of medical examinations: Nonetheless, eyeground-based diagnosis has not necessarily been employed as general means for diagnosing arteriosclerosis.

A conceivable reason for the above is that standards for diagnosing arteriosclerosis on the basis of photo-captured images of the eyeground are very complicated, and correct and proper eyeground-based diagnosis requires considerable clinical experience. In contrast, pursuit of convenience in eyeground-based diagnosis fails to attain sensitive detection of arteriosclerosis. At present, arteriosclerosis is diagnosed from photographs of the eyeground on the basis of "standards proposed by the hypertension research group in the Ministry of Education in 1969," "K-W classification," or "Scheie's classification," and over the years eyeground-based diagnosis has been gradually simplified. However, eyeground-based diagnosis has not yet become the first choice in clinical settings as some skill and experience is required.

In view of the foregoing, an object of the present invention is to provide non-invasive, simple and sensitive means for detecting arteriosclerosis.

SUMMARY OF THE INVENTION

<The Detection System of the Present Invention (Including the Electronic Detection System of the Present Invention Described Below)>

The present inventors have considered that arbitrary and discretionary photographing of the eyeground widely adopted in the conventional practice, is one factor that hampers proper assessment regarding the progress of arteriosclerosis. When an actual blood vessel undergoes pulsation, in order for blood to be efficiently pumped from the heart to the peripheries, surging involves a time-lag caused by the Windkessel phenomenon. Therefore, when the eyeground is photographed arbitrarily in an untimed manner, the photograph of the eyeground taken during a diastolic phase of the heart differs from that taken during a systolic phase of the heart due to the Windkessel phenomenon. As a result, precise measurement of diameters of the arteries and veins of the eyeground—which is required for the diagnosis of arteriosclerosis from a photograph of the eyeground—becomes difficult. The present inventors have focused attention on this problem to thereby attain the present invention.

Accordingly, the present invention provides an arteriosclerosis detection system comprising: electrocardiographic signal detection means; eyeground image detection means for detecting an eyeground image in synchronization with an electrocardiographic signal detected by the detection means; and eyeground vein constriction detection means for detecting the constriction of an eyeground vein in the vicinity of a site at which the eyeground vein and an eyegroud artery cross each other, on the basis of the eyeground image detected in synchronization with the electrocardiographic signal (hereinafter the system may be referred to as "the present detection system").

No particular limitation is imposed on the means for the electrocardiographic signal detection, so long as the means can detect an electrocardiographic signal accurately. For example, the detection means may be a device in which an electrode sensor containing a piezoelectric element is mounted on the chest or another site of a subject, to thereby detect the electrocardiographic signal. Typically, the mechanism of a conventional electrocardiograph may be employed as the electrocardiographic signal detection means.

No particular limitation is imposed on the electrocardiographic signal, so long as the signal can be identified as an established pattern of an electrocardiogram. The electrocardiographic signal may be any pattern selected from among a P wave, a Q wave, an R wave, an S wave, and a T wave. However, from practical point of view, the use of an R wave, which is a pattern signal detected when blood is fed from the heart to the entire body, or a T wave, which corresponds to recovery of ventricular activation, is recommended.

No particular limitation is imposed on leads for obtaining electrocardiographic signals from a subject, and "standardized 12 lead ECG" may be employed. Preferably, suitable leads are selected in accordance with the type of the above-selected electrocardiographic signal; i.e., leads that enable easy detection of the selected electrocardiographic signal are preferred. When an R wave is selected as an electrocardiographic signal, lead II, lead I, lead $_aV_L$, or lead $V_1$, in which the difference in electric potential between the left and right hands of a subject is measured, is preferably selected.

In the present detection system, "electrocardiographic signal identification means"—which is means for identifying electrocardiographic signals detected by the electrocardiographic signal detection means, extracting a specific pattern signal from the thus-identified signals as an electric signal, and transmitting the extracted specific pattern signal to the eyeground image detection means—is selectively employed when an electrocardiographic signal must be processed before an eyeground image is detected in synchronization with the electrocardiographic signal. If desired, the specific signal pattern may be subjected to, for example, amplification processing, which is preferably associated with the eyeground image detection means. As the electrocardiographic signal identification means, there may be employed an output terminal of a conventional electrocardiograph, which detects a specific electrocardiographic signal, such as an R wave, and transmits the signal as output.

As described above, the eyeground image detection means detects an eyeground image in synchronization with an electrocardiographic signal detected by the electrocardiographic signal detection means.

Within the context of the present invention, the word "synchronize" refers to the case where, with respect to a specific pattern of an electrocardiographic signal, the eyeground image detection means is caused to respond at a predetermined timing. For example, when an R wave, which is a typical wave pattern, is selected as an electrocardiographic signal, the eyeground image detection means is operated at an arbitrary point of the R wave. No particular limitation is imposed on the manner of determining the timing at which the eyeground image detection means is operated, so long as the cycle of the timing is shorter than that between a point at which an electrocardiographic signal rises and a point at which the same signal rises again (e.g., a timing between a point at which an R wave rises and a point at which the next R wave rises). Thus, when an eyeground image is detected under synchronization with an electrocardiographic signal, accurate data on eyeground blood vessels can be obtained; specifically, data on diameters of eyeground blood vessels which are necessary for determining an index of arteriosclerosis in the present invention can be obtained. As described above, when an eyeground photograph that has been taken at an arbitrary time is used, accurate measurement of the diameters of eyeground blood vessels—which vary with diastole and systole of the heart by virtue of the Windkessel phenomenon—is difficult. However, when an eyeground image is captured in synchronization with an electrocardiographic signal, an image of eyeground blood vessels can be captured at a certain timing with respect to a pulsation, resulting in accurate measurement of the diameters of eyeground blood vessels.

Typical examples of the eyeground image detection means include a camera with a mechanism capable of photographing the eyeground (specifically, a so-called fundus camera, which may be of analog type or digital type). In this case, the camera is operated such that releasing of the shutter for capturing the eyeground image is synchronized with emergence of a specific pattern of an electrocardiographic signal. Meanwhile, detecting an eyeground image by use of a digital video camera capable of continuously capturing an eyeground image as digital image data is suitable for the synchronization of the eyeground image described below with an electrocardiographic signal by use of a computer.

By use of the present detection system, an image of eyeground blood vessels can be obtained at a certain timing with respect to pulsation. When data obtained from the image of eyeground blood vessels are correlated with the progress of arteriosclerosis of a subject, arteriosclerosis of the subject can be detected. As used herein, the expression "detection of arteriosclerosis" refers to detection of the degree of organic change of the form of arteries of a subject and the degree of extensibility or functional change of the arteries; i.e., detection of the degree of flexibility (elasticity) of the arteries. Therefore, when progress of arteriosclerosis is recognized by the present detection system, arteries of a subject undergo organic change, elasticity and extensibility of the arteries are decreased, and flexibility of the arteries is lost to some extent. In such a case, for example, the possibility of an ischemic disease becomes high. No particular limitation is imposed on the specific means for the aforementioned correlation. Data on diameters of eyeground blood vessels are particularly important for detecting arteriosclerosis of a subject. When the data on diameters of eyeground blood vessels are compared with conventional arteriosclerosis diagnosis standards; for example, the aforementioned "standards proposed by the hypertension research group in the Ministry of Education in 1969," "K-W classification," or "Scheie's classification" arteriosclerosis of the subject can be detected.

The present inventors have found that the degree of constriction of an eyeground vein in the vicinity of an arteriovenous crossing site (as used herein the terms "eyeground artery" and "eyeground vein" refer to the medical terminology "retinal artery" and "retinal vein," respectively) can be used as a very useful index for establishing correlation with the progress of arteriosclerosis. The present detection system being capable of capturing an image of eyeground blood vessels at a certain timing with respect to pulsation, is very useful for obtaining the index.

The degree of constriction of an eyeground vein may be detected through direct visual observation of the image of the eyeground obtained by use of the present detection system. Eyeground vein constriction detection means for detecting the constriction of an eyeground vein may be provided in the aforementioned eyeground image detection means, and the detection process may be automated. Examples of the eyeground vein constriction detection means include software in which means for detecting data on the eyeground image—the data having been input by use of a scanner and converted into electronic data—is programmed (e.g., means for detecting a portion at which an eyeground vein and an eyeground artery cross each other and/or means for calculating the degree of constriction of an eyeground vein in the vicinity of a crossing site). When the aforementioned eyeground image data are processed by use of such software, reliable information in the degree of constriction of an eyeground vein can be conveniently detected.

Next will be described the degree of constriction of an eyeground vein, which the present inventors have found to be a useful index for determining the progress of arteriosclerosis.

At an arteriovenous crossing site (i.e., at a site at which these blood vessels cross each other), the eyeground artery and the eyeground vein are known to have a common outer membrane. When arteriosclerosis is found at such an arteriovenous crossing site, the inner wall of the eyeground artery is sclerosed, and "traction force" (including "shearing stress," the same shall apply hereinafter) attributed to the sclerosed intima of the artery causes constriction of the eyeground vein in the vicinity of the crossing site. The higher the degree of constriction caused by the traction force, the higher the degree of progress of arteriosclerosis in the vicinity of the crossing site.

The present inventors have found that the ratio of the outer diameter of an eyeground vein in the vicinity of an arteriovenous crossing site to that of an eyeground vein at a portion distant from the crossing site (i.e., the original outer diameter of the eyeground vein) (hereinafter the ratio will be referred to as "V ratio") is very useful as an index for the degree of constriction of the eyeground vein in the vicinity of the crossing site, the constriction being attributed to arteriosclerosis.

Specifically, V ratio is calculated as described below.

FIG. 1 is a schematic representation of an eyeground artery, and an eyeground vein which is constricted by means of a traction force. As shown in FIG. 1, an eyeground artery 10 and an eyeground vein 20 cross each other such that the vein runs beneath the artery, the intima of the eyeground artery 10 is sclerosed (not illustrated) in the vicinity of a crossing site 30, and the eyeground vein 20 is constricted in the vicinity of the crossing site 30 by means of a traction force attributed to the arteriosclerosis.

The outer diameter of the eyeground artery 10 is represented by "$\Phi A$"; the outer diameter of the eyeground vein 20 at a position about $3 \times \Phi A$ distant from the crossing site 30 toward the periphery of the vein is represented by "V2," the outer diameter being regarded as the outer diameter of the eyeground vein in the case where no constriction is observed at the crossing site 30; and the outer diameter of the eyeground vein 20 at a position near the eyeground artery 10 (e.g., at a position about $\frac{1}{10} \times \Phi A$ distant from the crossing site 30) is represented by "V1."

The ratio between V1 and V2 (typically V1/V2) is called V ratio. Low V ratio (V1/V2) shows progress of arteriosclerosis of the eyeground artery 10 in the vicinity of the crossing site 30; i.e., high risk of arteriosclerosis.

FIG. 2 schematically illustrates the case where screlosis of the intima of an eyeground artery 11 extends away from the crossing site 31 (screlosed portions: 111 and 112), one of the sclerosed portions being slightly distant from a crossing site 31. In this case, traction forces of different directions are applied to an eyeground vein 21 to thereby cause the eyeground vein 21 to dislocate in the vicinity of the crossing site 31.

In such a case, small amounts of correction must be applied to the aforementioned V ratio (V1/V2). Specifically, at the crossing site 31, when the length of a line indicated by 211 between the center axes of the eyeground vein 21 positioned on the left and right with respect to the eyeground artery 11 is 0.5 to 1.0 times the outer diameter of the eyeground vein 21, a correction value obtained by subtracting 0.1 from the aforementioned V ratio is employed for detection of arteriosclerosis. When the length of the vector line 211 is more than 1.0 times the outer diameter of the eyeground vein 21, a correction value obtained by subtracting 0.2 from the aforementioned V ratio is employed as the general V ratio for detection of arteriosclerosis.

Unlike the case of dislocation of the eyeground vein shown in FIG. 2, FIG. 3 illustrates the case where a certain angle is formed by the center axes of an eyeground vein positioned on one side (i.e., the peripheral side) and the other side with respect to an eyeground artery which crosses with the vein. Unlike the case shown in FIG. 2 where the center axes 221 and 222 of an eyeground vein 22 are not parallel, an example in FIG. 3 show set angle formed by the center axes 221 and 222 with respect to an eyeground artery 12 which crosses with the eyeground vein 22 where they are positioned on the peripheral side and the other side respectively. In this case, an angle which is formed by the center axis 222 and a line between a point at which the center axis 222 crosses with an outer diameter line 331 at a position about $\frac{1}{10} \times \Phi A$ distant from a crossing site 33 and a point at which the center axis 221 crosses with an outer diameter line 321 at a position about $\frac{1}{10} \times \Phi A$ distant from a crossing site 32 is defined as an offset angle $\alpha$.

In such a case also, the aforementioned V ratio (V1/V2) must be corrected to some extent. Specifically, a correction value obtained by subtracting S value—obtained by multiplying an offset angle $\alpha$ by $\frac{1}{100}$—from the aforementioned V ratio is employed as the general V ratio for detection of arteriosclerosis.

The offset angle $\alpha$ which is employed for such correction is preferably 10° (absolute value) or less, while angle of less than 5° (absolute value) is desirable.

As described above, in a preferred mode of the present detection system, regarding the degree of constriction of an eyeground vein in the vicinity of an arteriovenous crossing site, a general V ratio (which includes "V ratio" in the case where no dislocation and no offset angle are detected at the crossing site, and the aforementioned two types of correction are not employed. Hereinafter, unless otherwise specified, general V ratio includes V ratio to which no correction is applied) or a similar factor is calculated, and the thus-calculated value is correlated with the degree of arteriosclerosis, to thereby detect arteriosclerosis.

In the present detection system, in order to ensure an enhanced reliability of calculated values, preferably, general V ratios are measured in multiple cross section sites (at least two crossing sites, typically two or three crossing sites) of the eyeground arteries and the eyeground veins of a subject, the crossing sites being one papilla diameter or more distant from the optic papilla; the resultant general V ratios are averaged; and the average general V ratio is employed as an index for detecting arteriosclerosis of the subject.

Normalized data obtained by normalizing, in accordance with the ages of a plurality of subjects, the degree of constriction of an eyeground vein in the vicinity of a crossing site of the eyeground artery and an eyeground vein, which is obtained on the basis of general V ratio or a similar factor, can be correlated with the degree of constriction of each of the subjects, to thereby detect the degree of aging of the artery of the subject (i.e., blood vessel age).

<The Electronic Detection System of the Present Invention>

When an eyeground image is detected by the present detection system, the most preferred mode of the present detection system utilize software which can provide an eyeground image synchronized with an electrocardiographic signal by obtaining, by use of a computer, a stationary eyeground image synchronized with an arbitrary electrocardiographic signal from an animated eyeground image (hereinafter the software may be referred to as "the present software") (the mode may be referred to as "the present electronic detection system").

Accordingly, the present invention provides an arteriosclerosis detection system comprising: electrocardiographic signal detection means; eyeground image detection means for detecting an eyeground image in synchronization with an electrocardiographic signal detected by the detection means;

and eyeground vein constriction detection means for detecting the constriction of an eyeground vein in the vicinity of a site at which the eyeground vein and an eyeground artery cross each other, on the basis of the eyeground image detected in synchronization with the electrocardiographic signal, wherein detection of the eyeground image is carried out by implementing algorithm of software which can provide an eyeground image synchronized with an electrocardiographic signal by obtaining, by use of a computer, a stationary eyeground image synchronized with an arbitrary electrocardiographic signal from an animated eyeground image.

In the present electronic detection system, a motion eyeground image obtained by use of a digital video camera serving as the eyeground image detection means is input, as digital data, into a computer via a DV terminal (media converter is also available) and a DV capture card such as IEEE1394 card, EZDV (product of Canopus Co., Ltd.), DVRapter (product of Canopus Co., Ltd.), or DVRex (product of Canopus Co., Ltd.), with an electrocardiographic signal converted into a digital signal by use of an A/D converter being input into the computer. Subsequently, the input motion eyeground image data and the input electrocardiographic signal data are combined in parallel so as to synchronize the eyeground image data with the electrocardiographic signal data in the same frame, thereby obtaining digital synchronization data of the motion eyeground image data and the electrocardiographic signal. The digital synchronization data may be subjected to compression, so long as data required for performing the present electronic detection system are not lost. Coding such as compression may be performed by means of a coding format such as MPEG.

The resultant digital synchronization data may be recorded in, for example, a magnetic tape, a magnetic disk, CD-ROM, MO, or DVD-R. However, any data recording medium may be employed in accordance with transition and improvement of data recording technology.

A calculation value related to an eyeground image (e.g., the aforementioned general V ratio) is obtained by extracting a stationary image; i.e., a digital data per frame, from the above-obtained digital synchronization data.

The amount of change in calculation value (e.g., the below-described V ratio) on the basis of unit time can be obtained by use of stationary eyeground image data extracted from motion eyeground image data at a point in time "t" corresponding to an arbitrary electrocardiographic signal and stationary eyeground image data extracted from the motion eyeground image data at another point in time "t+$\Delta$t." As described below, the time "t" is preferably selected in accordance with an electrocardiographic signal which has been synchronized with a motion eyeground image.

When stationary image data are extracted from digital synchronization data of motion eye ground image data and electrocardiographic signal data while the motion eyeground image and the electrocardiographic image are displayed on display means such as a computer display, extraction operation can be visualized. Such visualization of extraction operation is preferred. Therefore, the present software preferably includes an algorithm of visualization means by use of, for example, a computer display.

In the present software, a desired algorithm can be formed by use of a typical computer programming language.

Examples of the computer programming language which may be employed include low-level languages such as a machine language and an assembly language; high-level languages such as Fortran, ALGOL, COBOL, C, BASIC, PL/1, Pascal, LISP, Prolog, APL, Ada, Smalltalk, C++, and Java; fourth generation languages; and end user languages. If desired, special purpose languages may be employed.

No particular limitation is imposed on the electronic medium in which the present software can be stored, and the software may be stored in, for example, a magnetic tape, a magnetic disk, CD-ROM, MO, or DVD-R. The present invention also provides an electronic medium including the present software. In addition to the aforementioned media, any data recording medium may be employed in accordance with transition and improvement of data recording technology.

In the present detection system, since eyeground image data can be extracted under synchronization with an electrocardiographic signal at an arbitrary timing, calculation values corresponding to different electrocardiographic signals, which are obtained by executing the algorithm of the present software, are easily consolidated. For example, in order to enhance reliability of calculation value, preferably, general V ratios of eyeground images corresponding to an R wave and a T wave of a subject, which are electrocardiographic signals, are consolidated so as to obtain an average value, and the average general V ratio is employed as an index for detecting arteriosclerosis of the subject.

When an algorithm—which correlates, through comparison, normalized data obtained by normalizing, in accordance with the ages of a plurality of subjects, the degree of constriction of an eyeground vein in the vicinity of a crossing site of the eyeground artery and an eyeground vein, which is obtained on the basis of V ratio or a similar factor, with the degree of constriction of each of the subjects—is incorporated into the present software, and when organic change of the form of the artery and pulsation of the artery are functionally evaluated, the degree of aging of the artery of the subject (i.e., blood vessel age) can be detected. For example, when the general V ratio of a subject is higher than normalized data obtained on the basis of the ages and sexes of subjects, arteriosclerosis of the subject is determined to proceed as compared with the normalized data, and the blood vessel age (in terms of organic change of the form of artery and pulsation of the artery) of the subject is evaluated to be higher than the actual age of the subject. In contrast, when the general V ratio of a subject is lower than normalized data obtained on the basis of the ages and sexes of subjects, arteriosclerosis of the subject is determined not to proceed as compared with the normalized data, and the blood vessel age (in terms of organic change of the form of artery and pulsation of the artery) of the subject is evaluated to be lower than the actual age of the subject.

In one preferred mode of the present detection system, an algorithm capable of calculating the rate of change in calculation values corresponding to different electrocardiographic signals is incorporated in the present software.

The aforementioned rate of change can be obtained on the basis of the difference between calculation values, such as general V ratios, which correspond to eyeground images detected under synchronization with two different electrocardiographic signals serving as target signals. Typically, the difference between general V ratios corresponding to eyeground images detected under synchronization with the peak of an R wave and the end of a T wave, which are conspicuous in the pulsation cycle of the heart, is employed as an index for the aforementioned rate of change in calculation values.

The amount of change in general V ratio on the basis of unit time may be obtained as the rate of change in the general V ratio. In the case where general V ratio is represented by "y," the initial measurement time of the general V ratio is represented by "t," and the time between the initial measurement time and the next measurement time of the general V ratio is represented by "Δt," when the "Δt" is reduced such that the function of the general V ratio "y" and the time "t"; i.e., y=f(t), can be approximated to the linear function f(t)=at+b, the absolute value of the gradient "a" may be employed as the rate of change in the general V ratio. In this case, when the rate of change is high, blood vessels exhibit elasticity, whereas when the rate of change is low, blood vessels exhibit no elasticity and are sclerosed. The rate of change in general V ratio can be employed as a factor for functionally evaluating pulsation of blood vessels. When elasticity of blood vessels is recognized by means of execution of the aforementioned algorithm, the blood vessels are evaluated to be excellent in terms of organic change of the form of the vessels and pulsation of the vessels. In contrast, when arteriosclerosis of blood vessels is recognized by means of execution of the aforementioned algorithm, the blood vessels are evaluated to be poor in terms of organic change of the form of the vessels and pulsation of the vessels.

In the present electronic detection system, the time "t" may be determined arbitrarily. However, the amount of change in general V ratio on the basis of unit time varies in a certain cycle of the cycle of blood vessel pulsation of a subject, due to the Windkessel phenomenon. Therefore, in order to accurately correlate change of general V ratio with the degree of progress of arteriosclerosis, the time "t" is specified by use of an electrocardiographic signal with which an eyeground image has been synchronized; the eyeground image is caused to depend on the electrocardiographic signal, serving as a standard of the cycle of pulsation; and error in measurement of the amount of change in general V ratio within the cycle of pulsation is eliminated. The time "t" must be determined in accordance with the electrocardiographic signal with which the eyeground image has been synchronized. Preferably and practically, the time "t" is determined on the basis of an R wave or a T wave, which is a typical wave signal of an electrocardiographic signal. The aforementioned difference between general V ratios corresponding to the peak of an R wave and the end of a T wave is calculated when the "t" is determined at the peak of the R wave and the end of the T wave, and "Δt" is determined to be the time from the peak of the R wave and the end of the T wave or the time from the end of the T wave to the peak of the next R wave. The difference between general V ratios within Δt determines the rate of change in blood vessel pulsation, which is employed as an index for detecting the degree of arteriosclerosis.

BRIEF DESCRIPTION OF THE DRAWINGS

FIG. 6K is the eleventh segment of the flowchart illustrating the present software employed in the computer processing apparatus of the present electronic detection system.

DETAILED DESCRIPTION OF THE PREFERRED EMBODIMENT

Embodiments of the present invention will next be described.

<The Present Detection System>

Figure 1:
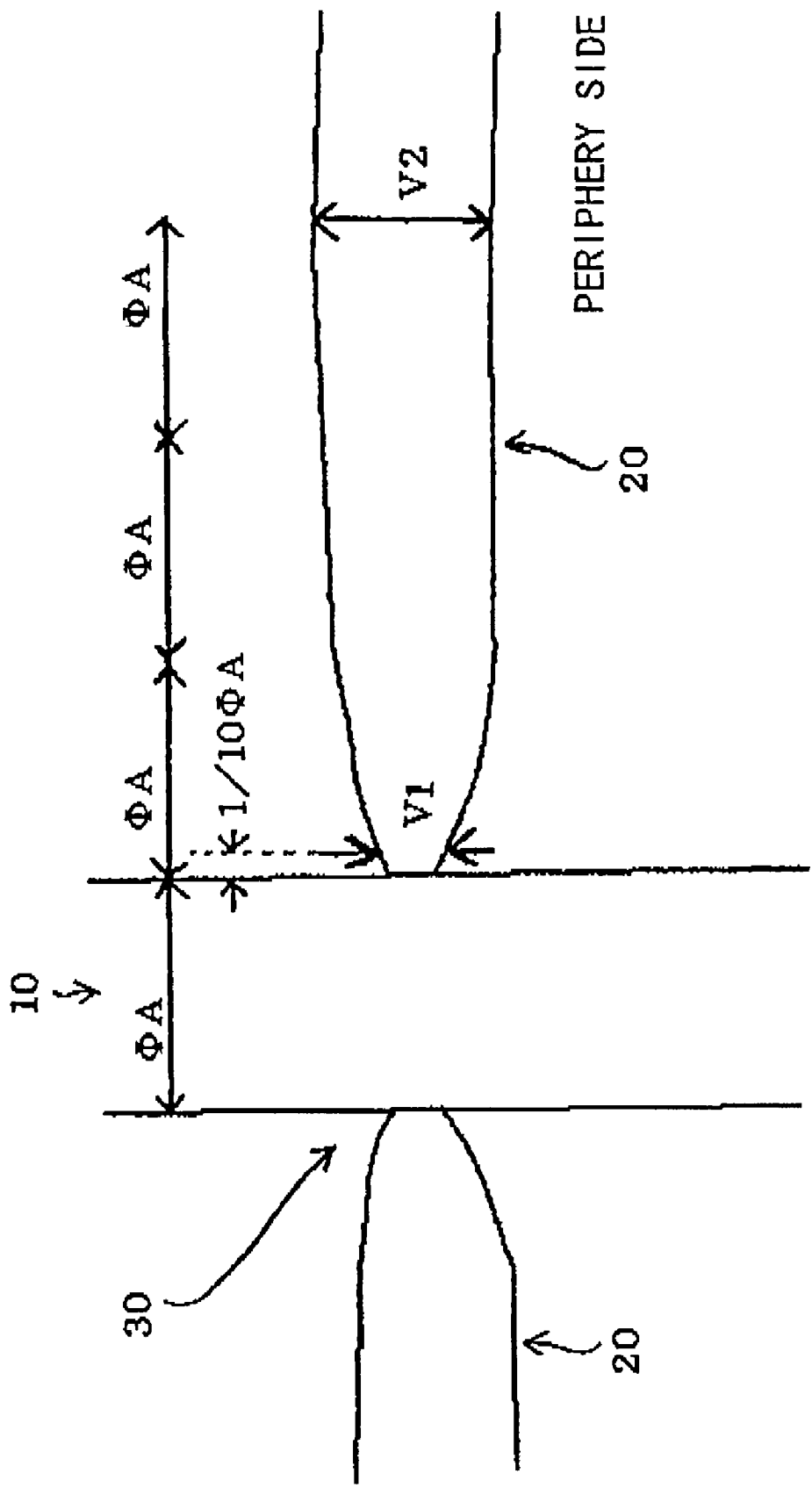
FIG. 1 is a schematic representation of an eyeground artery and an eyeground vein, which is constricted by means of a traction force.
Figure 2:
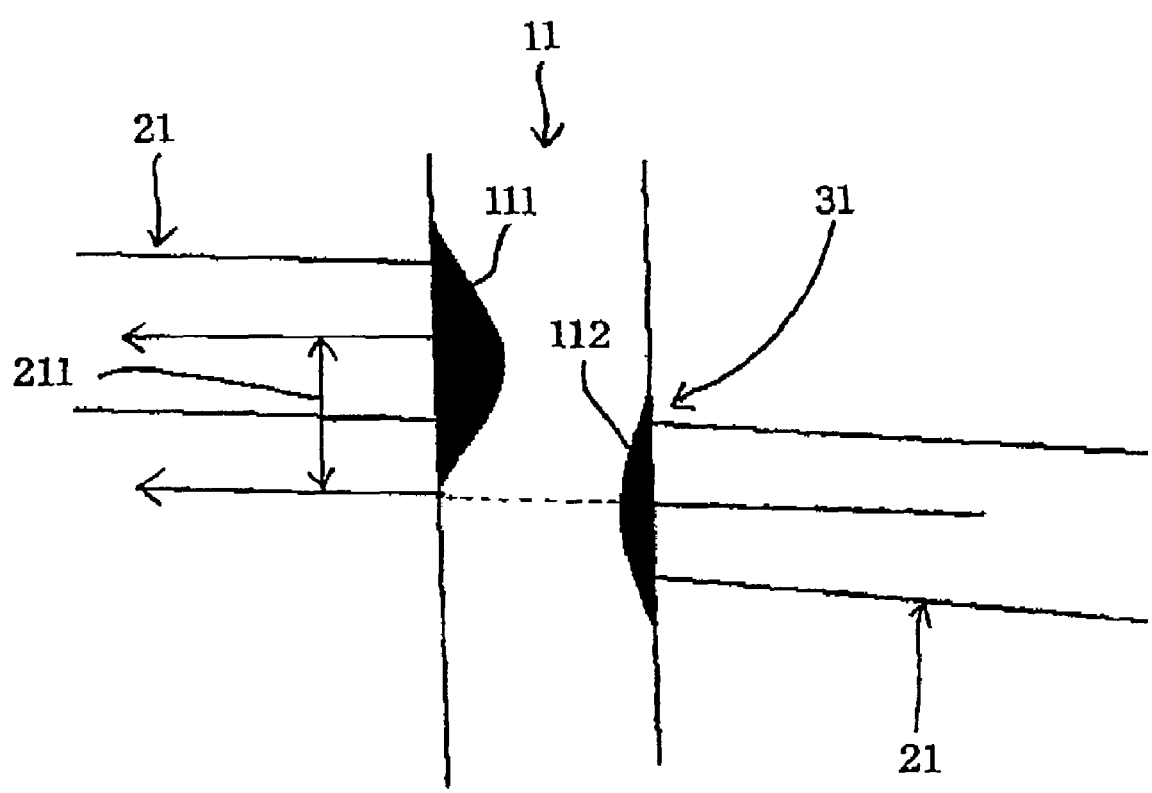
FIG. 2 is a schematic representation showing the case where screlosis of the intima of an eyeground artery extends away from the crossing site.
Figure 3:
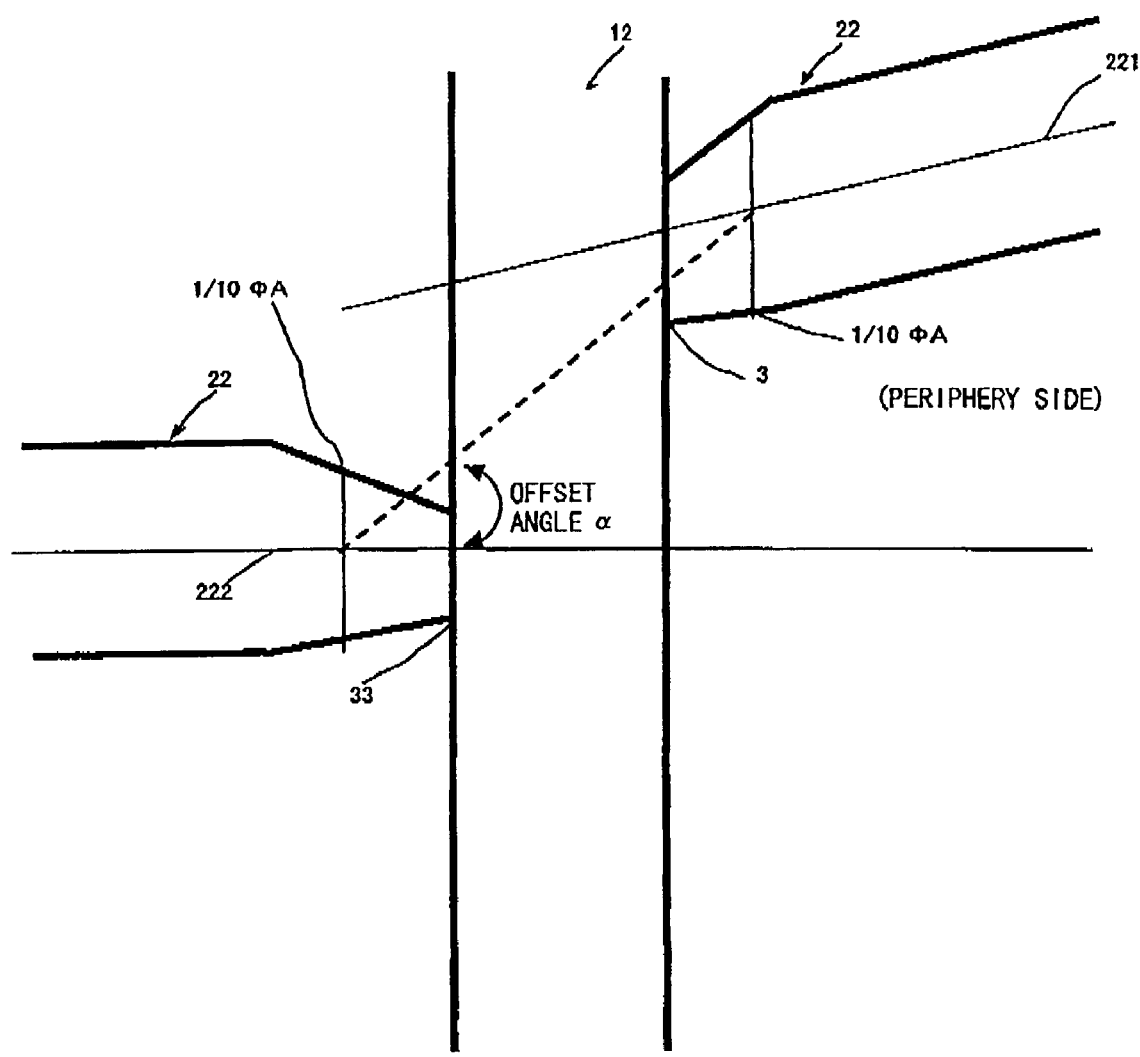
FIG. 3 is a schematic representation showing the case where an offset angle is detected in an eyeground vein at a site at which the eyeground vein and an eyeground artery cross each other.
Figure 4:
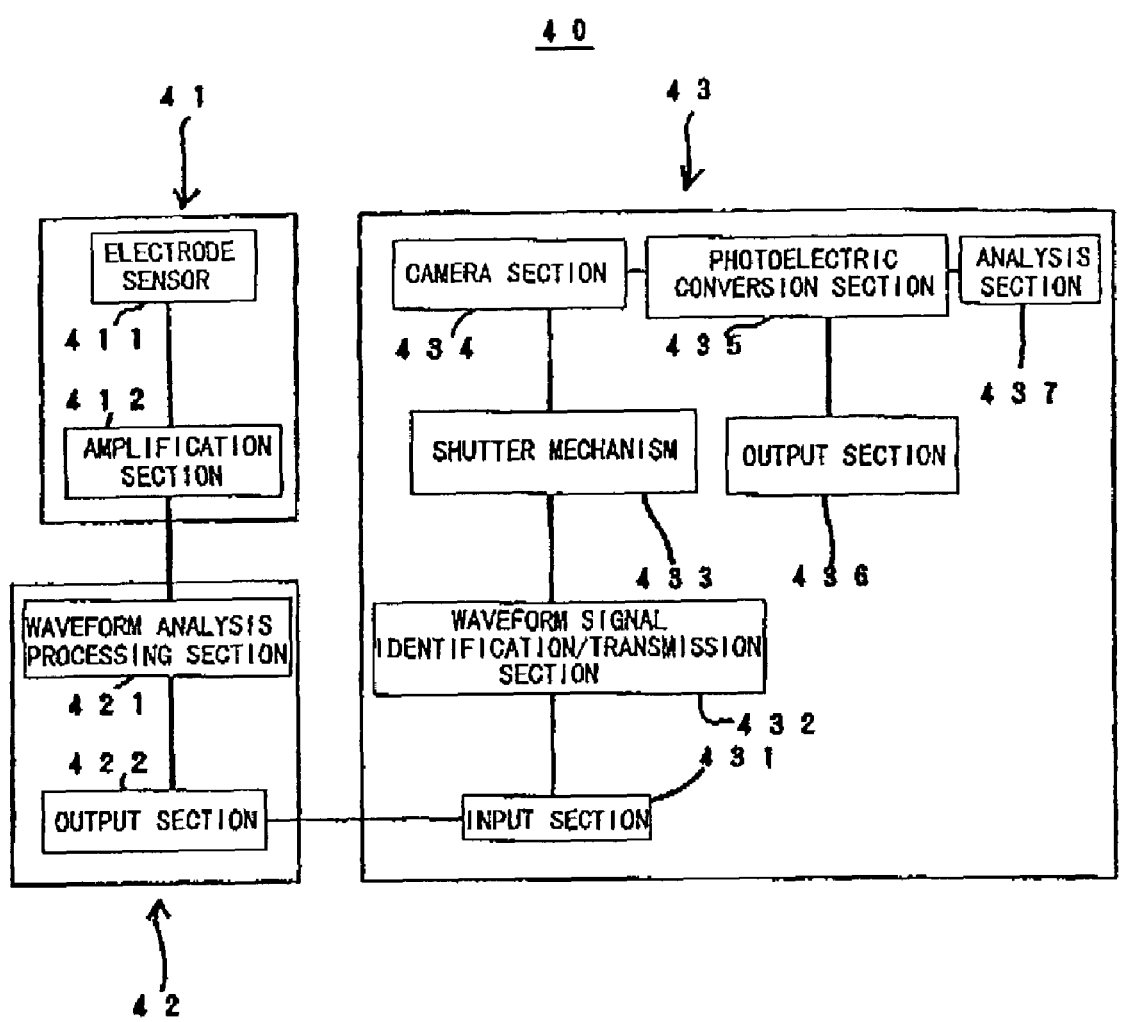
FIG. 4 is a block diagram showing the structure of the present detection system.

FIG. 4 is a block diagram showing an embodiment of the present detection system.

As shown in FIG. 4, the present detection system 40 includes an electrocardiographic signal detection unit 41, an electrocardiographic signal identification unit 42, and an eyeground image detection unit 43.

The electrocardiographic signal detection unit 41 includes an electrode sensor 411 and an amplification section 412. The electrocardiographic signal identification unit 42 includes a waveform analysis processing section 421 and an output section 422. The eyeground image detection unit 43 includes an input section 431, a waveform signal identification/transmission section 432, a shutter mechanism 433, a camera section 434, a photoelectric conversion section 435, an output section 436, and an analysis section 437.

The electrode sensor 411 of the electrocardiographic signal detection unit 41 contains, for example, a piezoelectric element. The electrode sensor 411 is a mechanism which is mounted on the chest or another site of a subject, to thereby detect the output electrocardiographic signal. The amplification section 412 is a mechanism for amplifying the electrocardiographic signal detected by the electrode sensor 411.

The waveform analysis processing section 421 of the identification unit 42 is a mechanism for selecting from the electrocardiographic signal amplified by the amplification section 412 pulse waves required in the present invention. For example, when a pulse wave signal of an R wave is sent to the below-described shutter mechanism 433 at a specific timing, the waveform analysis processing section specifically selects a specific pulse wave of the R wave at a specific timing with respect to an arbitrary point of the R wave (e.g., a rising point of the R wave). The waveform analysis processing section 421 may include selective amplification means, such as a filter amplifier, for specifically amplifying a pulse wave signal of a specific electrocardiographic signal corresponding to a specific timing. If desired, the waveform analysis processing section 421 may include an A/D conversion mechanism for digitizing an electrocardiographic signal (an analog signal) selectively amplified by the selective amplification means.

The output section 422 is a mechanism (e.g., an output terminal) for outputting to the eyeground image detection unit 43 an electrocardiographic signal selectively amplified in the waveform analysis processing section 421.

The input section 431 of the eyeground image detection unit 43 is a mechanism (e.g., an input terminal) for inputting to the detection unit a selectively amplified electrocardiographic signal output from the output section 422. The waveform signal identification/transmission section 432 is a mechanism for identifying an electrocardiographic signal inputted by means of the input section 431, and transmitting the signal as an appropriate ON/OFF signal to the shutter mechanism 433. The shutter mechanism 433 includes means for responding to the "ON" signal of the ON/OFF signal (e.g., a pulse signal corresponding to a specific electrocardiographic signal) to thereby operate the camera section 434, and for responding to the "OFF" signal (e.g., a signal other than the above signal) to thereby stop the operation of the camera section 434. Therefore, the camera section 434 is operated at a timing synchronized with a specific electrocardiographic signal, to thereby photograph the eyeground of a subject. If desired, the camera section 434 includes a mechanism employed in a typical eyeground camera for photographing the eyeground of a subject, such as an eyepiece, a light source, an alignment mechanism, or a view angle adjustment mechanism.

Optical data of an eyeground image which has been photographed in the camera section 434 synchronized with a specific electrocardiographic signal are converted to electrical data (which may be analog data or digital data) in the photoelectric conversion section 435. The resultant electrical data (e.g., a monitored image or a printed image) are output through the output section 436, and a photographed eyeground image is provided to a measurer. When the electrical data are subjected to appropriate analysis in the analysis section 437, the aforementioned eyeground image data can be converted to more useful data. Examples of the useful data include the general V ratio of a subject and the blood vessel age of the subject. The analysis section 437 includes appropriate software; for example, software for selecting an appropriate crossing site of an eyeground artery and an eyeground vein, software for calculating general V ratio at the crossing site, or software for calculating blood vessel age on the basis of the general V ratio.

As described above, in use of the present detection system 40, an electrocardiographic signal of a subject is detected in the electrocardiographic signal detection unit 41; a specific pulse wave such as an R wave is selected from the electrocardiographic signal at a specific timing in the electrocardiographic signal identification unit 42; and the resultant electrical signal is synchronized with the eyeground image detection means. Therefore, a reliable eyeground image which is not affected by the Windkessel phenomenon can be obtained in the eyeground image detection unit 43. When data on the basis of the reliable eyeground image are subjected to appropriate processing treatment, which is optionally performed as desired, data in relation to arteriosclerosis of a subject can be obtained.

<The Present Electronic Detection System>

Figure 5:
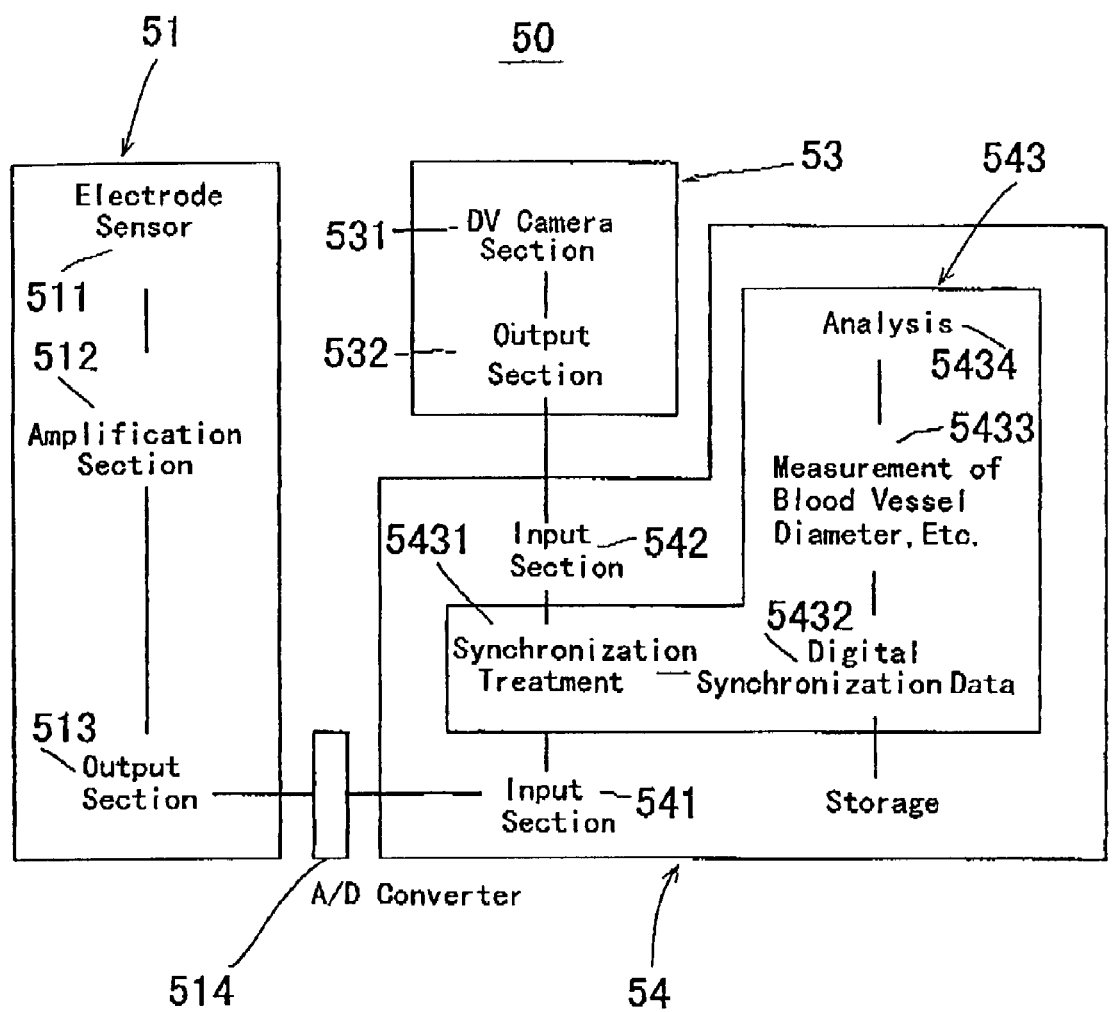
FIG. 5 is a block diagram showing the structure of the present electronic detection system.

FIG. 5 is a block diagram showing an embodiment of the electronic detection system of the present invention.

The present electronic detection system 50 includes an electrocardiographic signal detection unit 51, an eyeground image detection unit 53, and a computer 54.

The present electronic detection system 50 is an embodiment of the arteriosclerosis detection system of the present invention, in which an electrocardiographic signal is synchronized with an eyeground image by use of the computer 54.

The electrocardiographic signal detection unit 51 includes an electrode sensor 511, an amplification section 512, and an output section 513. The eyeground image detection unit 53 includes a DV camera section 531 and an output section 532.

The electrode sensor 511 of the electrocardiographic signal detection unit 51 contains, for example, a piezoelectric element. The electrode sensor 511 is a mechanism which is mounted on the chest or another site of a subject, to thereby detect the output electrocardiographic signal. The amplification section 512 is a mechanism for amplifying the electrocardiographic signal detected by the electrode sensor 511. The output section 513 is a mechanism for outputting the amplified electrocardiographic signal.

In the present electronic detection system 50, since synchronization treatment is performed in the computer 54, an electrocardiographic signal is transmitted from the output section 513 of the electrocardiographic signal detection unit 51 directly to an input section 541 of the computer 54. The electrocardiographic signal is preferably subjected to digitization treatment by use of, for example, an A/D converter 514.

In the eyeground image detection unit 53, an eyeground image of a subject is obtained by means of the digital video camera (DV camera) section. An motion image signal is extracted from the resultant eyeground image, and the motion image signal is output from the output section 532 via a DV terminal, and input to the computer 54 through the input section 542 via, for example, a DV capture card. A digital video camera included in the digital video camera section 531, which is employed for measuring subtle change in the diameter of an eyeground vein, preferably has the highest possible resolution. Specifically, the digital video camera preferably has a resolution of at least 2,000,000 pixels. If desired, the DV camera section 531 includes a mechanism employed in a typical eyeground camera for photographing the eyeground of a subject, such as an eyepiece, a light source, an alignment mechanism, or a view angle adjustment mechanism.

The motion eyeground image digital signal input to the computer 54 and the motion eyeground image signal input through the input section 541 are combined in parallel in a processing apparatus 543 of the computer 54 so as to synchronize motion eyeground image data with an electrocardiographic signal in the same frame (synchronization treatment 5431), thereby obtaining digital synchronization data (5432) of the motion eyeground image data and the electrocardiographic signal. If desired, the synchronization data 5432 may be subjected to, for example, compression.

Preferably, the digitized electrocardiographic signal and/or the motion eyeground image digital signal are subjected to reverse-quantization and interpolation, and then displayed or output as an electrocardiogram and/or an eyeground image by means of display means of the computer 54.

As described above, the synchronization data obtained in step 5432 may be employed in a step for measuring the diameter of an eyeground vein. Alternatively, the synchronization data obtained in step 5432 may be temporarily stored in an electronic medium.

A fundamental data measurement step 5433 is a step for selecting, as a target site, at least one site at which an eyeground vein and an eyeground artery cross each other, on the basis of the synchronization data obtained in step 5432; and for measuring fundamental data, such as the diameter of the eyeground vein and the eyeground artery at the target site, which are employed for detecting arteriosclerosis.

Fundamental data are preferably measured at different target sites at different timings. The timing may be arbitrarily selected, so long as change in data such as a change in the diameter of the blood vessels can be detected.

In an analysis step 5434, fundamental data measured in the fundamental data measurement step 5433, such as the diameter of an eyeground artery and an eyeground vein at a target site; i.e., at an arteriovenous crossing site, are subjected to appropriate analysis to thereby convert the fundamental data to more useful data. Examples of the useful data include the general V ratio of a subject, and the blood vessel age of the subject.

In the case where fundamental data are measured at a target site at different timings, when a change in general V ratio; i.e., a change in the diameter of an eyeground vein between the timings at the target site, is measured, the change in the general V ratio depending on an electrocardiographic signal on the basis of unit time can be calculated. As described above, measurement of the change in the general V ratio enables calculation of the degree of organic change of the blood vessels of a subject and the degree of flexibility of the arteries of the subject.

As described above, in use of the present electronic detection system 50, an eyeground image synchronized with an electrocardiographic signal in the computer 54; i.e., a reliable eyeground image which is not affected by the Windkessel phenomenon, can be continuously obtained. When data employed as indexes for detecting arteriosclerosis, such as general V ratio, are obtained, and the consolidation value of the data is calculated, reliability of the resultant general V ratio or a similar factor can be enhanced. In addition, indexes in relation to organic change of the blood vessels of a subject and to flexibility of the arteries of the subject can be easily obtained.

FIG. 6A through FIG. 6L show the flowchart (500) of the present software employed in the processing apparatus of the computer 54 of the present electronic detection system 50. In each process, if desired, the computer 54 is preferably operated by use of a mouse. (hereinafter operation by use of a mouse may be referred to as "mouse operation").

Figure 6A:
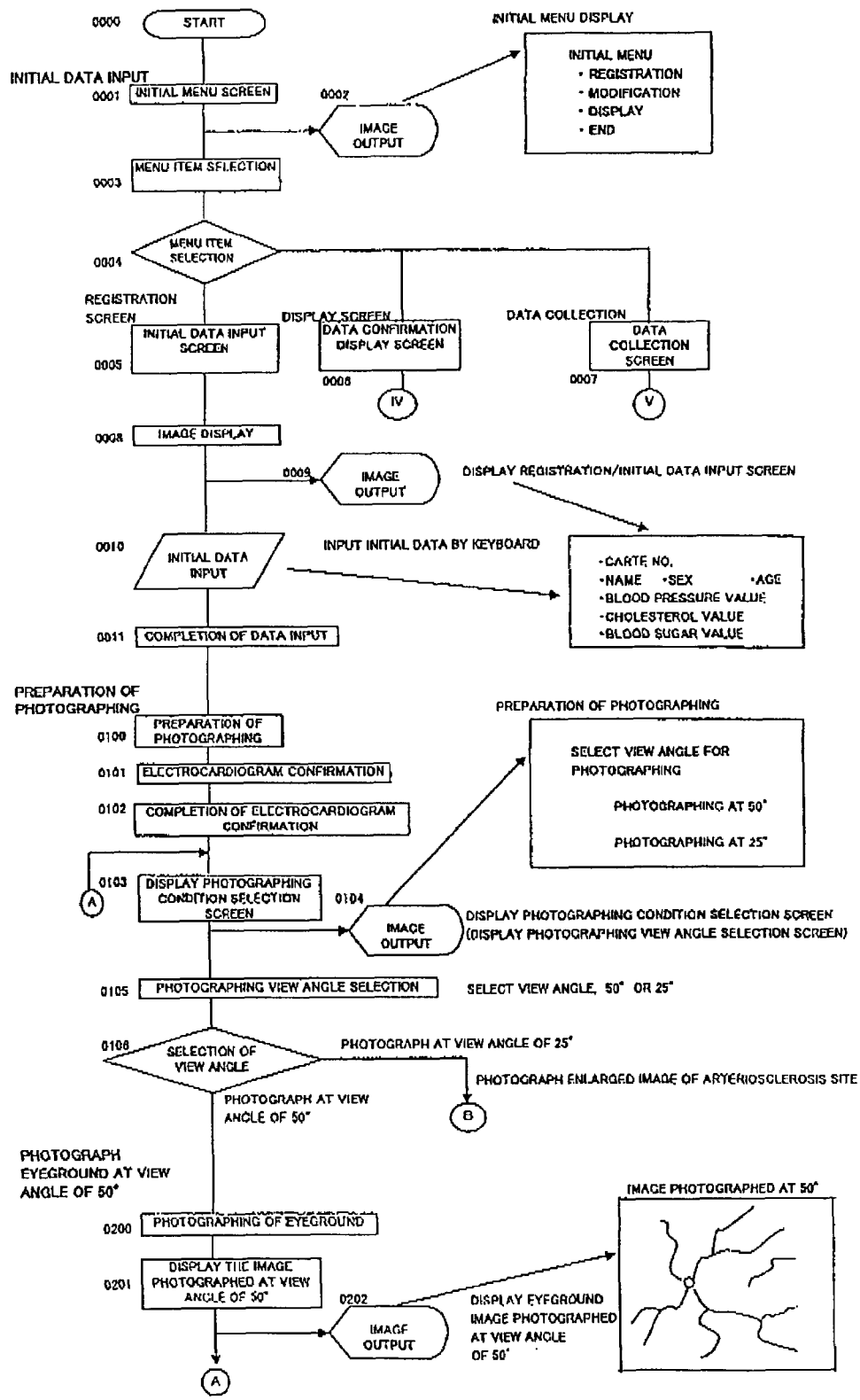
FIG. 6A is the first segment of the flowchart illustrating the present software employed in the computer processing apparatus of the present electronic detection system.

As shown in FIG. 6A, at 0000 "start," the computer 54 is set up such that the present software can execute the process shown in the flowchart 500. After setup, an initial menu screen is displayed (0001), image data are output by display means of the computer 54, and operation menu items, such as "registration," "modification," "display," "collection," and "end," are displayed on the screen (0002).

Subsequently, an initial menu is selected (0003). In an initial menu selection step (0004), when "registration" is selected and initial data are input, an "initial data input screen" is displayed (0005). When "display" is selected, a "data confirmation display screen" is displayed (0006). When "collection" is selected, a "data collection screen" is displayed (0007). Processes (IV) and (V) performed after selection of "display" or "collection" are described below. When "modification" is selected, a modification menu for modifying data is displayed. When "end" is selected, execution of the program is ended after execution of a process for confirming "end."

After the initial data input screen is displayed (0008, 0009), initial data (e.g., chart No., name, sex, age, blood pressure value, cholesterol value, and blood sugar value) are input by use of, for example, a keyboard (0010), to thereby complete input of initial data (0011).

An eyeground image photographing preparation process will be described next. First, the eyeground image detection unit 53 is prepared for photographing an eyeground image (0100), and an electrocardiographic signal input to the computer 54 through the input section 541 is recognized on the display of the computer 54 (0101).

After recognition of the electrocardiographic signal is complete (0102), a photographing condition selection screen is displayed (0103), a view angle (50° or 25°) for photographing an eyeground image is selected in the eyeground image detection unit 53, and photographing conditions are determined in the detection unit 53 in accordance with the selected view angle (0105, 0106).

When the view angle is selected to 50° in step 0106 (photographing process A), an eyeground is photographed at a view angle of 50° the eyeground image detection unit 53 (0200), digital data of the image are input to the computer 54 through the input section 542, and the image data are output by the display means of the computer (0201, 0202). The input eyeground image digital data and the electrocardiographic signal are combined in parallel so as to synchronize motion eyeground image data with the electrocardiographic signal in the same frame, thereby obtaining digital synchronization data of the motion eyeground image data and the electrocardiographic signal. After the photographing process A is complete, if desired, the photographing condition selection display process (0103) can be performed, to thereby execute the photographing process A repeatedly. After the photographing process A is complete, in order to obtain an enlarged image of a specific site, a process including a photographing process at a view angle of 25° (photographing process B) may be performed.

Figure 6B:
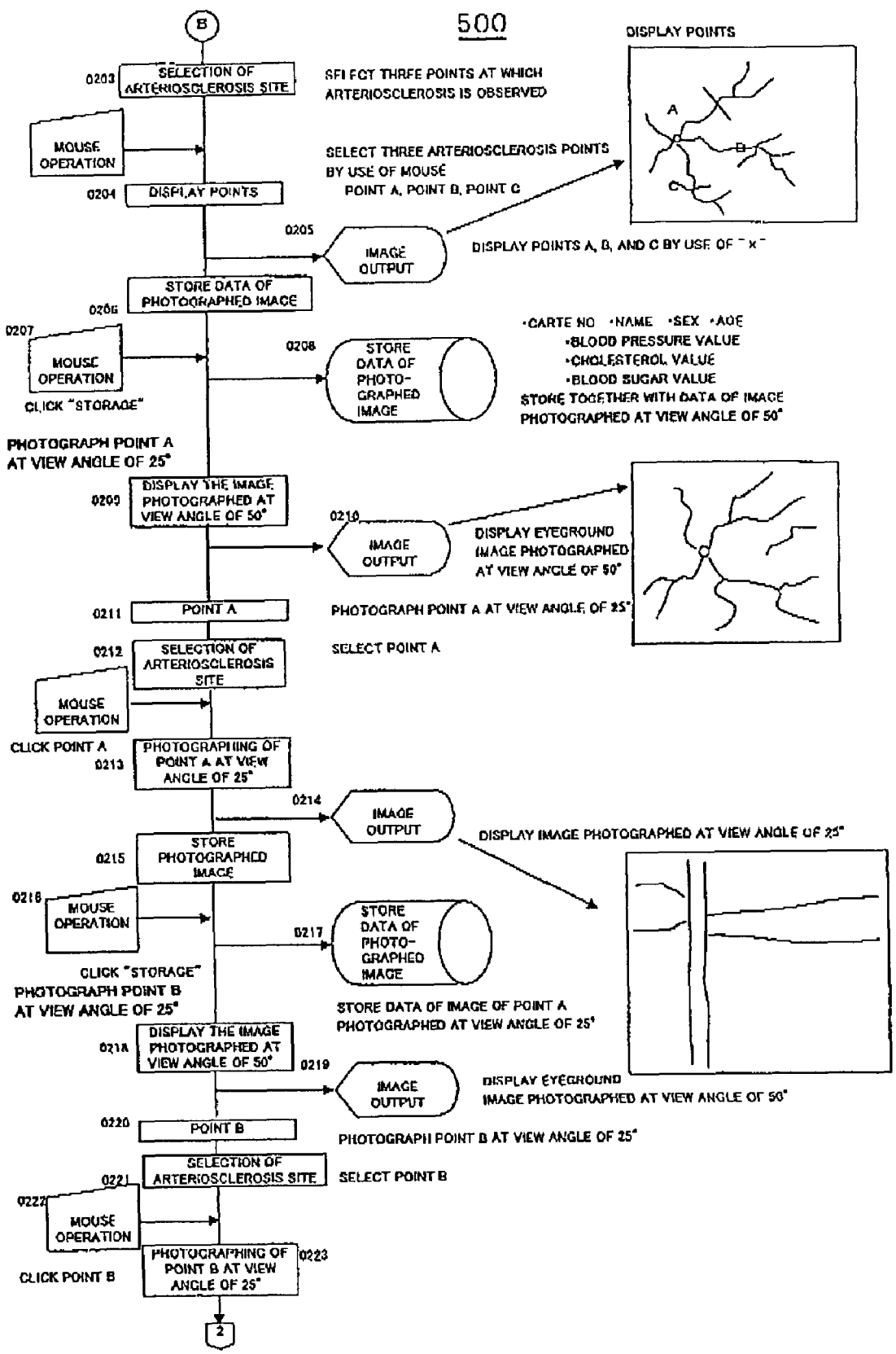
FIG. 6B is the second first segment of the flowchart illustrating the present software employed in the computer processing apparatus of the present electronic detection system.
Figure 6C:
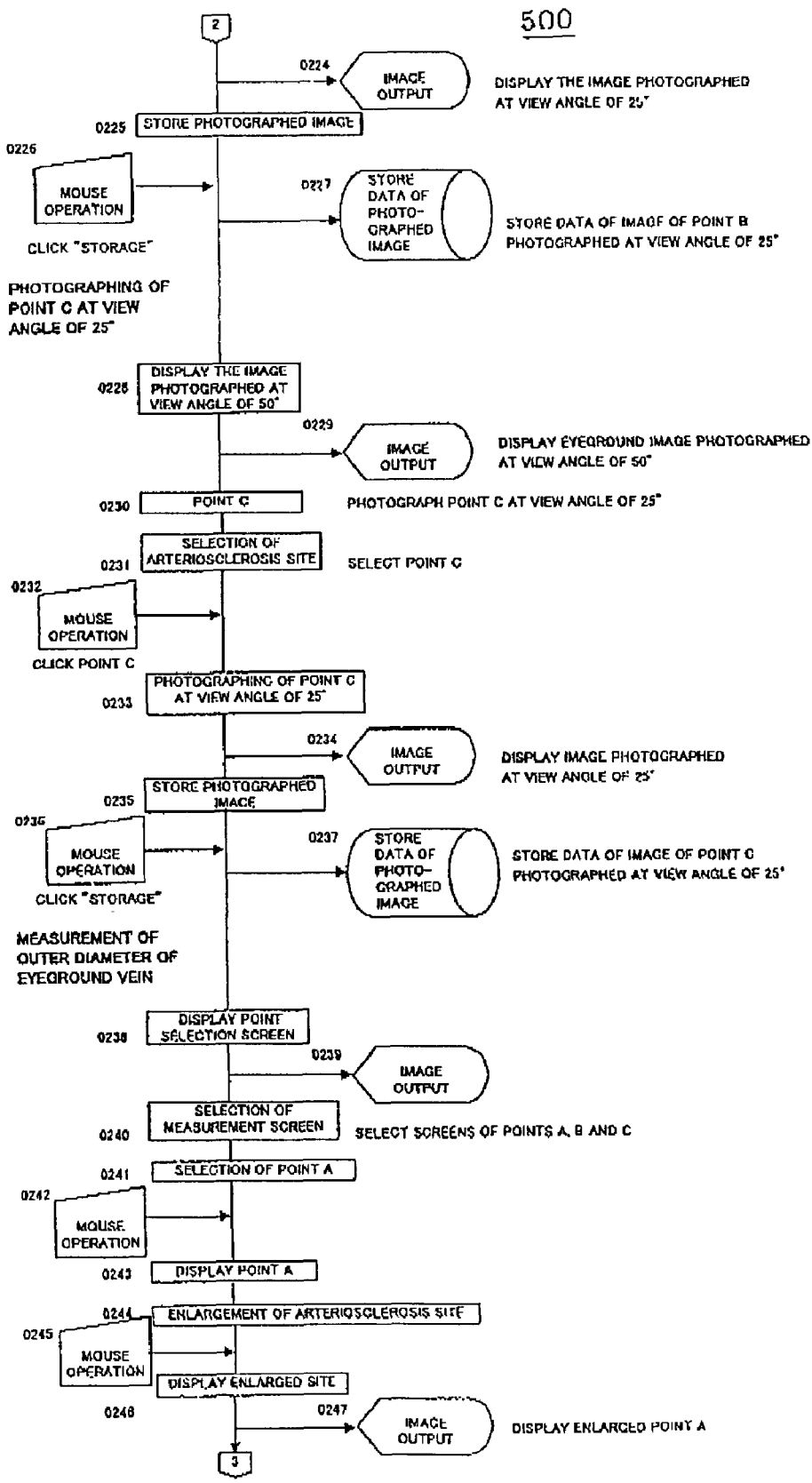
FIG. 6C is the third segment of the flowchart illustrating the present software employed in the computer processing apparatus of the present electronic detection system.

FIGS. 6B and 6C show a portion of the photographing process at a view angle of 25°. Firstly, three points at which arteriosclerosis is observed (e.g., point A, point B, and point C) are selected from the eyeground image photographed at a view angle of 50° (0203). When these points are selected, image data are output, and these points are displayed by use of the symbol "x" (0204, 0205). After these points are selected, data of the eyeground image photographed at each of the points at a view angle of 50°—synchronized with a specific electrocardiographic signal—are stored (0207, 0208). In this case, preferably, the aforementioned initial data, such as chart No. and blood pressure value, are stored together with the data of the photographed eyeground image.

Subsequently, in order to analyze the above-selected point A, the aforementioned eyeground image photographed at a view angle of 50° is displayed (0209, 0210); the vicinity of point A is photographed at a view angle of 25° (0211); a mouse is operated for selecting an arteriosclerosis site at point A (0212); the selected arteriosclerosis site is photographed at a view angle of 25° (0213); the resultant image of point A photographed at a view angle of 25° is output (0214); and the resultant image data are stored (0215 through 0217).

Subsequently, a process including output of the eyeground image photographed at a view angle of 25° and storage of the resultant image data is performed at point B or point C in a manner similar to that employed in the case of point A (point B: 0218 through 0227, point C: 0228 through 0237).

A process in relation to measurement of the outer diameter of an eyeground vein will next be described (FIG. 6C). Firstly, a point selection screen is displayed (0238). Specifically, image data of the point selection screen are output (0239). Here, a measurement point is selected from the above-selected points; i.e., point A, point B, and point C (0240). When point A is selected (0241), point A is displayed on a measurement screen through mouse operation (0242, 0243), an arteriosclerosis site is enlarged by means of mouse operation (0244), and image data of the enlarged site are output (0245 through 0247).

Figure 6D:
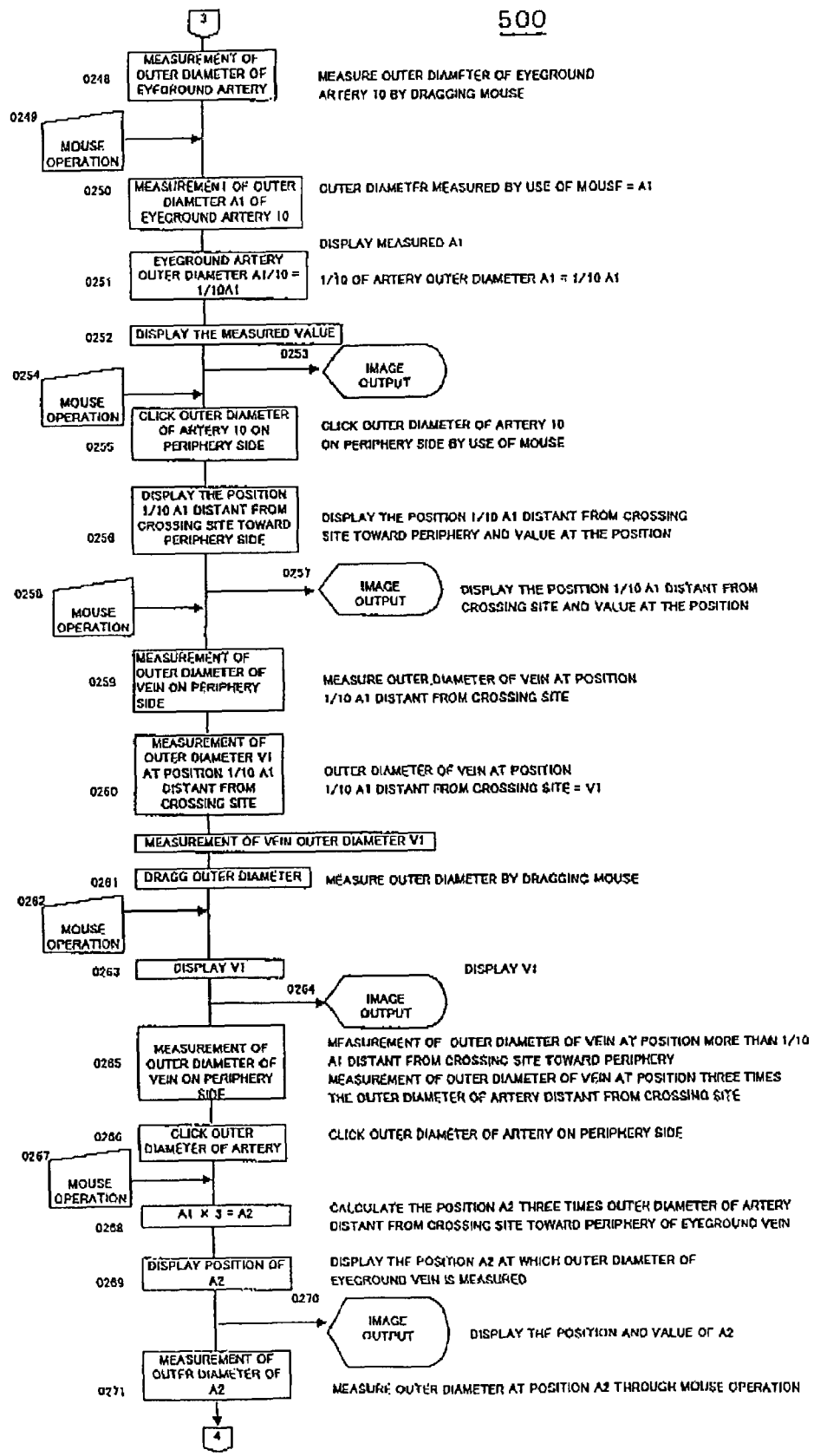
FIG. 6D is the fourth segment of the flowchart illustrating the present software employed in the computer processing apparatus of the present electronic detection system.
Figure 6E:
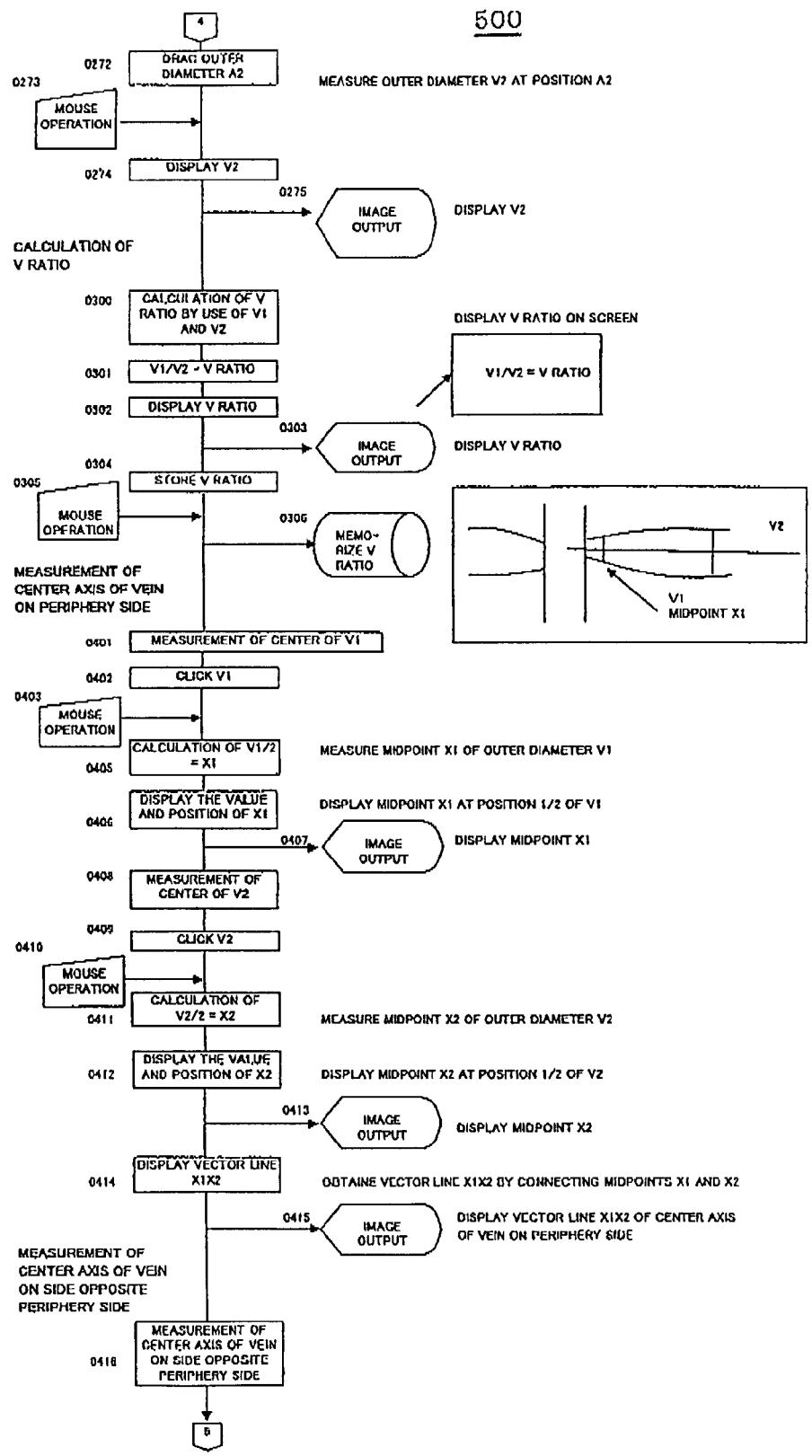
FIG. 6E is the fifth segment of the flowchart illustrating the present software employed in the computer processing apparatus of the present electronic detection system.

Subsequently, a step for measuring the outer diameter of an eyeground artery is performed (FIG. 6D). Measurement of the outer diameter of an eyeground artery only at point A will next be described. However, the measurement step can be performed at points B and C.

The eyeground artery outer diameter measurement step (0248) is performed by displaying the aforementioned enlarged site at point A, and dragging the outer diameter of an eyeground artery 10 to be measured by use of a mouse (0249). The outer diameter of the eyeground artery 10 is measured (0250) and displayed as "A1" (0252), and a value equal to 1/10 the outer diameter A1 is displayed as "1/10 A1" (0251). Thereafter, image data of the aforementioned site are output (0253), and the outer diameter of the eyeground artery 10 on the periphery side of the eyeground vein at the arteriovenous crossing site is clicked (0255). Subsequently, the position 1/10 A1 distant from the crossing site toward the periphery of the eyeground vein and the value at the position are displayed (0256), and image data of the position and the value are output (0257).

Subsequently, a first eyeground vein outer diameter measurement step (0259) is performed. After the image data are output (0257), an outer diameter (V1) of the eyeground vein at a position 1/10 A1 distant from the crossing site toward the periphery is measured by dragging a mouse, and image data of the outer diameter are output while V1 is displayed (0260 through 0264).

Subsequently, an eyeground vein outer diameter measurement step (0265) is performed at a position more than 1/10 A1 distant from the crossing site toward the periphery. Firstly, the outer diameter of the eyeground artery on the periphery side of the eyeground vein at the arteriovenous crossing site is clicked (0266). The eyeground artery outer diameter A1 is multiplied by 3 to thereby obtain "A2." A position of the eyeground vein A2 distant from the crossing site toward the periphery and the value at the position are displayed, and image data of the position and the value are output (0267 through 0270).

Subsequently, a second eyeground vein outer diameter measurement process (0271) is performed. After the image data are output, an outer diameter (V2) of the eyeground vein at a position A2 distant from the crossing site toward the periphery is measured by dragging a mouse (0272, 0273) (FIG. 6E), and image data of the outer diameter are output (0275) while V2 is displayed (0274).

Subsequently, a V ratio calculation process (0300) is performed. On the basis of the above-obtained V1 and V2, V ratio (V1/V2) is calculated (0301), an image of the V ratio is displayed (0302, 0303), and data of the V ratio are stored (0303 through 0306).

Subsequently, a process for measuring the center axis of the eyeground vein on the periphery side (0401) is performed. In this process, firstly, V1 is clicked (0402, 0403), and V1 is multiplied by ½ to thereby calculate X1 (0405). Subsequently, image data of the midpoint (X1) of a line segment obtained by dragging V1 on the basis of the thus-calculated X1 are output (0406, 0407). In addition, V2 is clicked (0408, 0409), and V2 is multiplied by ½ to thereby calculate X2 (0410, 0411). Subsequently, image data of the midpoint (X2) of a line segment obtained by dragging V2 on the basis of the thus-calculated X2 are output (0412, 0413). Finally, a vector line X1X2 formed by connecting the midpoints X1 and X2 is displayed (0414), and image data of the line X1X2 are output (0415).

Subsequently, a process for measuring the center axis of the eyeground vein on the side opposite the periphery side (0416) is performed. This process is performed in a manner substantially identical with that of the aforementioned measurement process (0401).

Figure 6F:
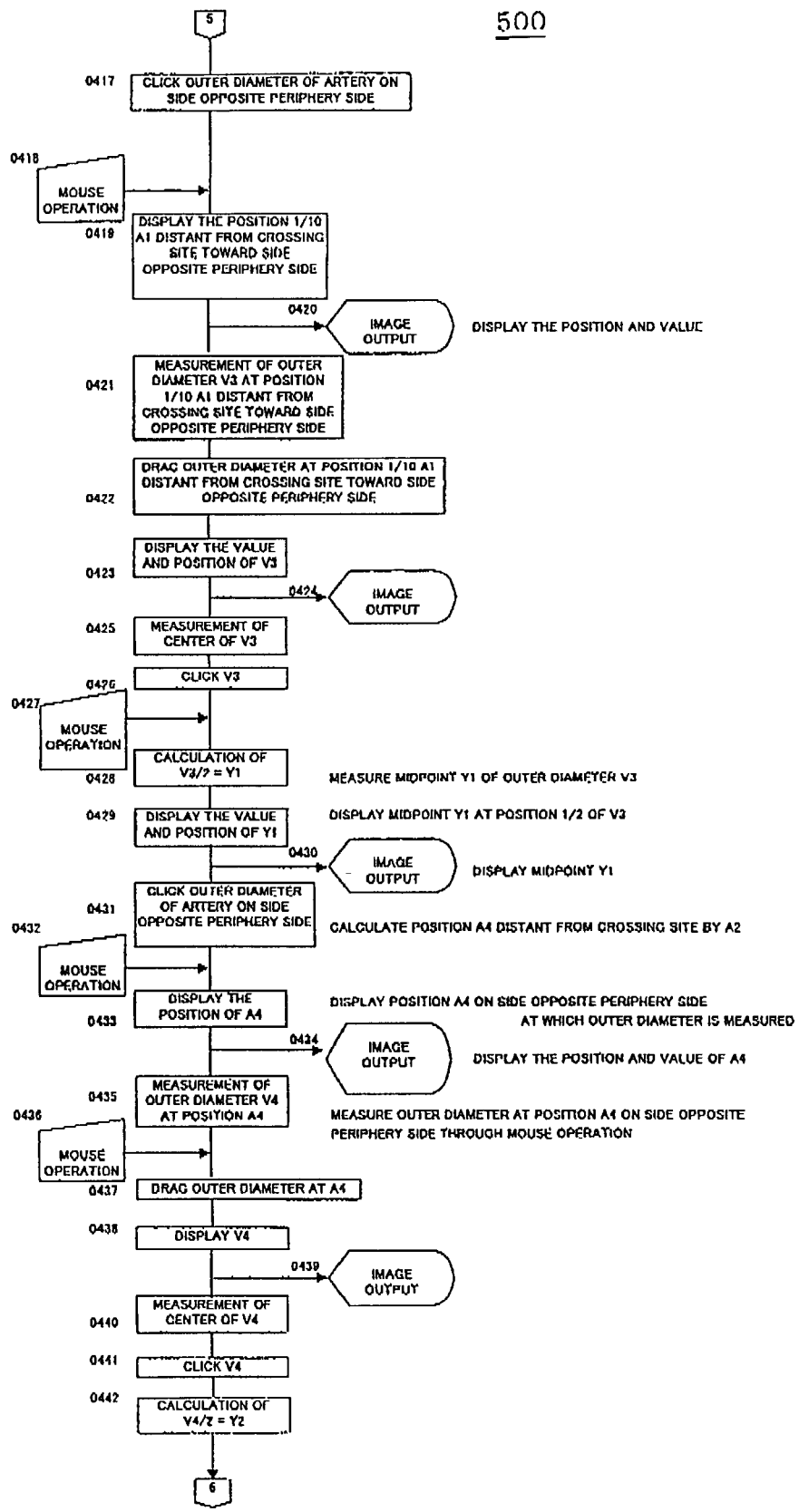
FIG. 6F is the sixth segment of the flowchart illustrating the present software employed in the computer processing apparatus of the present electronic detection system.

Firstly, at the arteriovenous crossing site of point A, the outer diameter of the eyeground artery on the side opposite the periphery side of the eyeground vein is clicked (0417) (FIG. 6F). Subsequently, the position 1/10 A1 distant from the crossing site toward the side opposite the periphery of the eyeground vein and the value at the position are displayed (0418, 0419), and image data of the position and the value are output (0420).

Subsequently, an outer diameter (V3) of the eyeground vein at a position 1/10 A1 distant from the crossing site toward the side opposite the periphery is measured by dragging a mouse (0421, 0422), and image data of the outer diameter are output while V3 is displayed (0423, 0424). Furthermore, in order to measure the center of V3 (0425), V3 is clicked (0426, 0427), and V3 is multiplied by ½ to thereby calculate Y1 (0428). Subsequently, image data of the midpoint (Y1) of a line segment obtained by dragging V3 on the basis of the thus-calculated value of Y1 are output (0429, 0430).

Figure 6G:
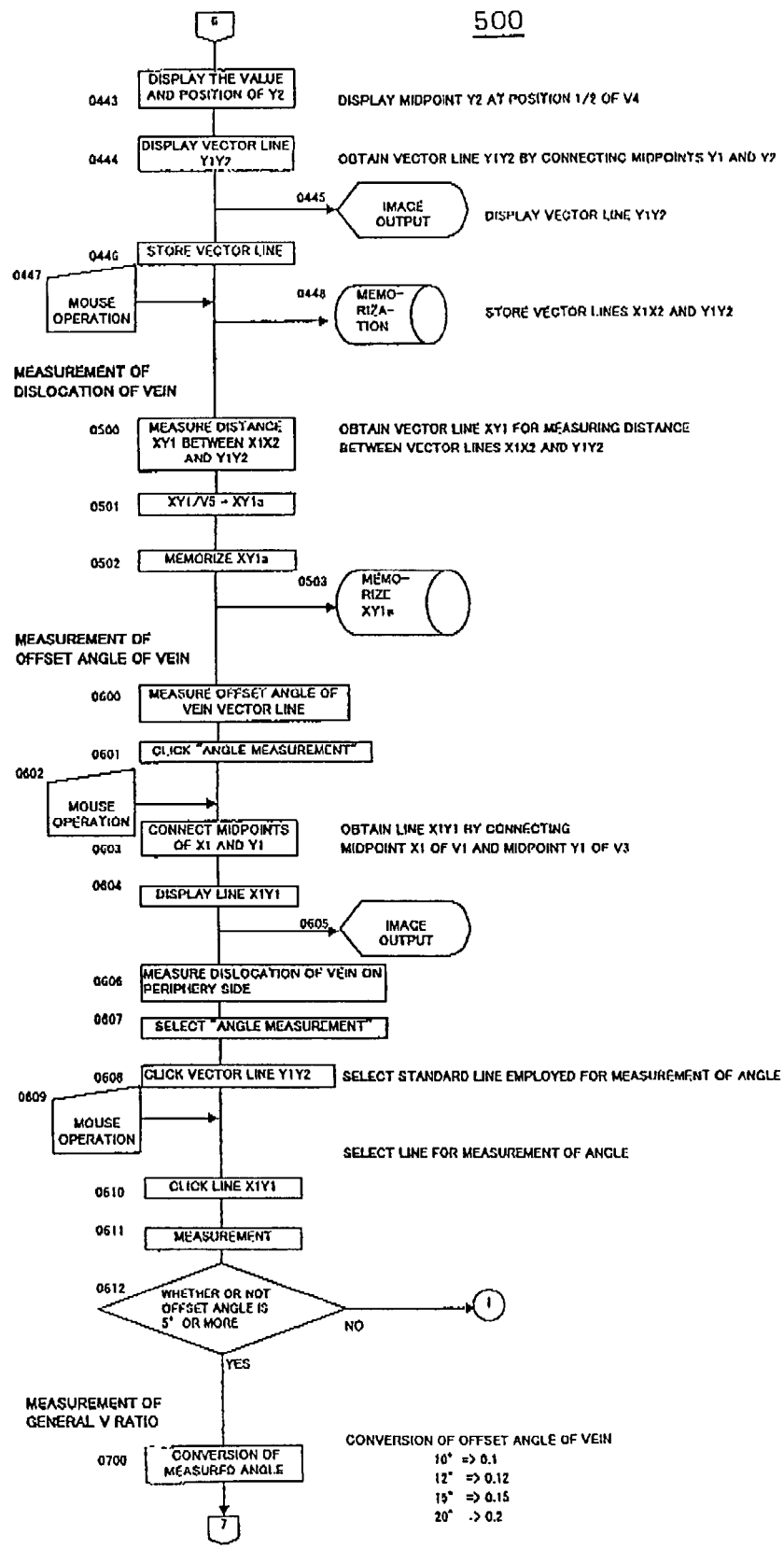
FIG. 6G is the seventh segment of the flowchart illustrating the present software employed in the computer processing apparatus of the present electronic detection system.

Subsequently, a position (A4) A2 distant from the crossing site toward the side opposite the periphery is displayed through mouse operation (0431, 0432), and an outer diameter (V4) of the eyeground vein at the position A4 is measured (0435). Specifically, V4 is measured by dragging a mouse (0436, 0437), and image data of the outer diameter are output while V4 is displayed (0438, 0439). Furthermore, V4 is clicked (0440, 0441), and V4 is multiplied by ½ to thereby calculate Y2 (0442). Subsequently, image data of the midpoint (Y2) of a line segment obtained by dragging V4 on the basis of the thus-calculated value of Y2 are output (0443). Finally, a vector line Y1Y2 formed by connecting the midpoints Y1 and Y2 is displayed, and image data of the line X1X2 are output (0444, 0445) (FIG. 6G).

The above-obtained vector lines X1X2 and Y1Y2 are stored as data (0446 through 0448).

Subsequently, an eyeground vein dislocation measurement process for calculating general V ratio is performed.

Firstly, the average distance between the vector line X1X2 and the vector line Y1Y2 is calculated as XY1 (0500). Subsequently, XY1 is divided by the eyeground vein diameter (average of V4 and V2:V5); i.e., XY1/V5=XY1a is calculated (0501), and XY1a is stored (0502, 0503).

Subsequently, an eyeground vein offset angle measurement process (0600) is performed. "Angle measurement" is selected from a menu and clicked (0601), X1 is connected to Y1 through mouse operation (0602, 0603) to thereby form a vector line X1Y1, and image data of the vector line X1Y1 are output (0604, 0605). In order to measure dislocation of the eyeground vein on the periphery side (0606), "angle measurement" is selected from a menu and clicked (0607), the vector line Y1Y2 serving as a standard line for measuring offset angle is clicked (0608), the vector line X1Y1 is selected through mouse operation (0609, 0610), and the angle (absolute value) formed by the vector lines Y1Y2 and X1Y1 is measured (0611).

When in step 0612 the resultant offset angle (absolute value) is determined to be 5° or more (YES), a general V ratio measurement process (offset angle correction process) is performed by use of the offset angle as a correction factor.

Figure 6H:
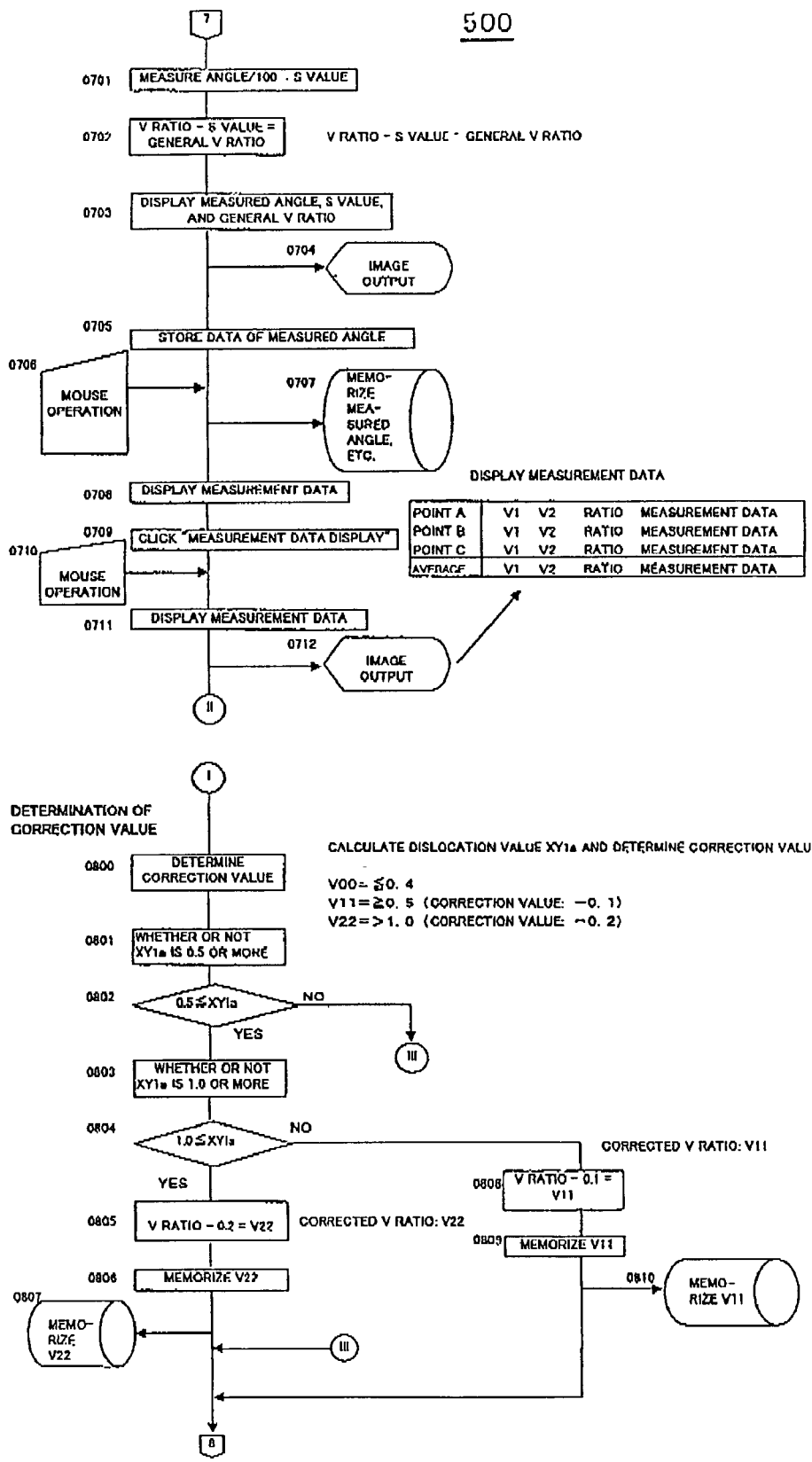
FIG. 6H is the eighth segment of the flowchart illustrating the present software employed in the computer processing apparatus of the present electronic detection system.

In the offset angle correction process (0700), the angle formed by the vector lines Y1Y2 and X1Y1—which is measured in the aforementioned angle measurement process—is employed as a correction parameter of V ratio, the angle is converted to an appropriate value (S value), and V ratio is corrected by use of the value, to thereby measure general V ratio. Firstly, the measured angle/100 is calculated (0701) (FIG. 6H). For example, when the measured angle is 10°, S value becomes 0.1, and when the measured angle is 15°, S value becomes 0.15. Subsequently, S value is subtracted from V ratio to thereby obtain "general V ratio" (0702), and the measured angle, S value, and general V ratio are displayed and image data of the these values are output (0703, 0704). In order to store data of the measured angle, etc., (0705), data of the measured angle, etc. are memorized (0707) through mouse operation (0706).

The measurement data obtained through the aforementioned processes may be displayed (0708). When "display of measurement data" is clicked by use of a mouse (0709, 0710), the above-obtained measurement data are displayed (0711, 0712). The data include V1, V2, V ratio, general V ratio, etc. at point A; V1, V2, V ratio, general V ratio, etc. at point B; and V1, V2, V ratio, general V ratio, etc. at point C. Thus, the offset angle correction process is performed. After the offset angle correction process is complete, the below-described "process for comparing measured general V ratio with normalized data" (process (II)) is performed.

When in step 0612 the offset angle is determined to be less than 5° (NO), the below-described general V ratio measurement process (dislocation correction process) (process (I)) is performed.

In the general V ratio measurement process (0800) (dislocation correction process), V ratio is corrected on the basis of XY1a calculated in step 0501, to thereby obtain general V ratio.

In steps 0801 and 0802, a determination is made as to whether or not XY1a is 0.5 or more. When XY1a is determined to be less than 0.5 (i.e., NO), a correction value becomes 0, and data of V ratio calculated in the step 0301 are stored (process (III)). In contrast, when XY1a is determined to be 0.5 or more (i.e., YES), a step for determining whether or not XY1a is 1.0 or more (0803, 0804) is performed. In step 0804, when XY1a is determined to be at least 0.5 and less than 1.0 (i.e., NO), a correction value becomes −0.1. In this case, a value obtained by subtracting 0.1 from V ratio calculated in step 0301 (V11:0808) becomes an accurate value corresponding to the degree of progress of arteriosclerosis, and the value is memorized as general V ratio V11 and stored (0809, 0810). In step 0804, when XY1a is determined to be 1.0 or more (i.e., YES), a correction value becomes −0.2. In this case, a value obtained by subtracting 0.2 from V ratio calculated in step 0301 (V22:0805) becomes an accurate value corresponding to the degree of progress of arteriosclerosis, and the value is memorized as general V ratio V22 and stored (0806, 0807). Thus, the dislocation correction process is performed. After the dislocation correction process is complete, the below-described "process for comparing measured general v ratio with normalized data" is performed.

Figure 6I:
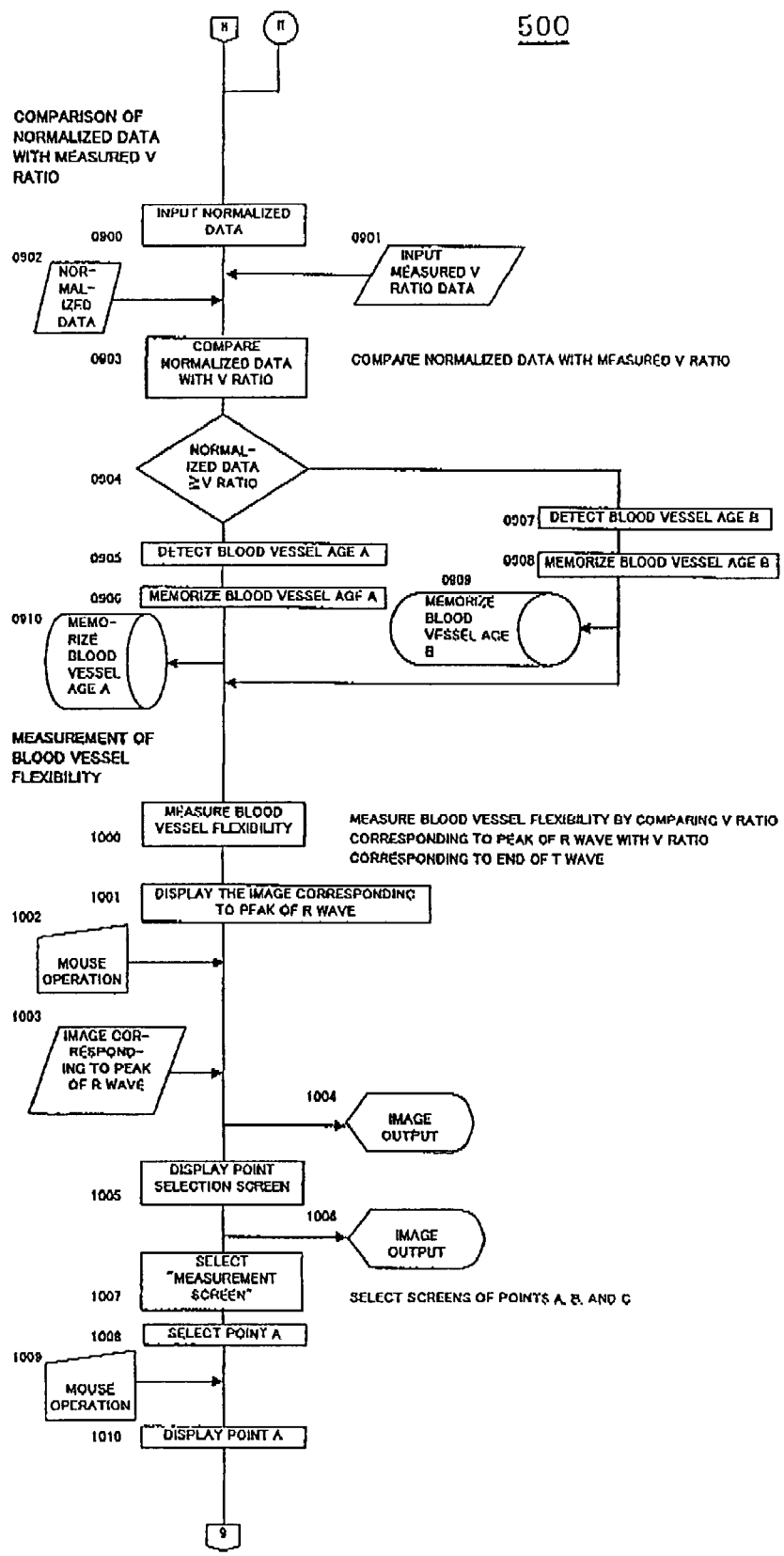
FIG. 6I is the ninth segment of the flowchart illustrating the present software employed in the computer processing apparatus of the present electronic detection system.

Next will be described the process for comparing measured general V ratio with normalized data (0900) (FIG. 6I).

Input normalized data (normalized data of general V ratio obtained in accordance with age) (0902) are compared (0903) with data of the above-measured general V ratio (0901). In step 0904, the normalized data are compared with the general V ratio data. When the general V ratio data are determined to be less than the normalized data (i.e., NO), a blood vessel age is detected to be younger than the actual age of a subject (0907), and the blood vessel age is stored as blood vessel age B (0908, 0909). In contrast, when the general V ratio data are determined to be equal to or greater than the normalized data (i.e., YES), a blood vessel age is detected to be equal to or older than the actual age of a subject (0905), and the blood vessel age is stored as blood vessel age A (0906, 0910).

Subsequently, a blood vessel flexibility measurement process (1000) is performed. In the process, general V ratios are obtained on the basis of an eyeground image synchronized with the peak of an R wave and an eyeground image synchronized with the end of a T wave, and these V ratios are compared, to thereby measure blood vessel flexibility.

Figure 6J:
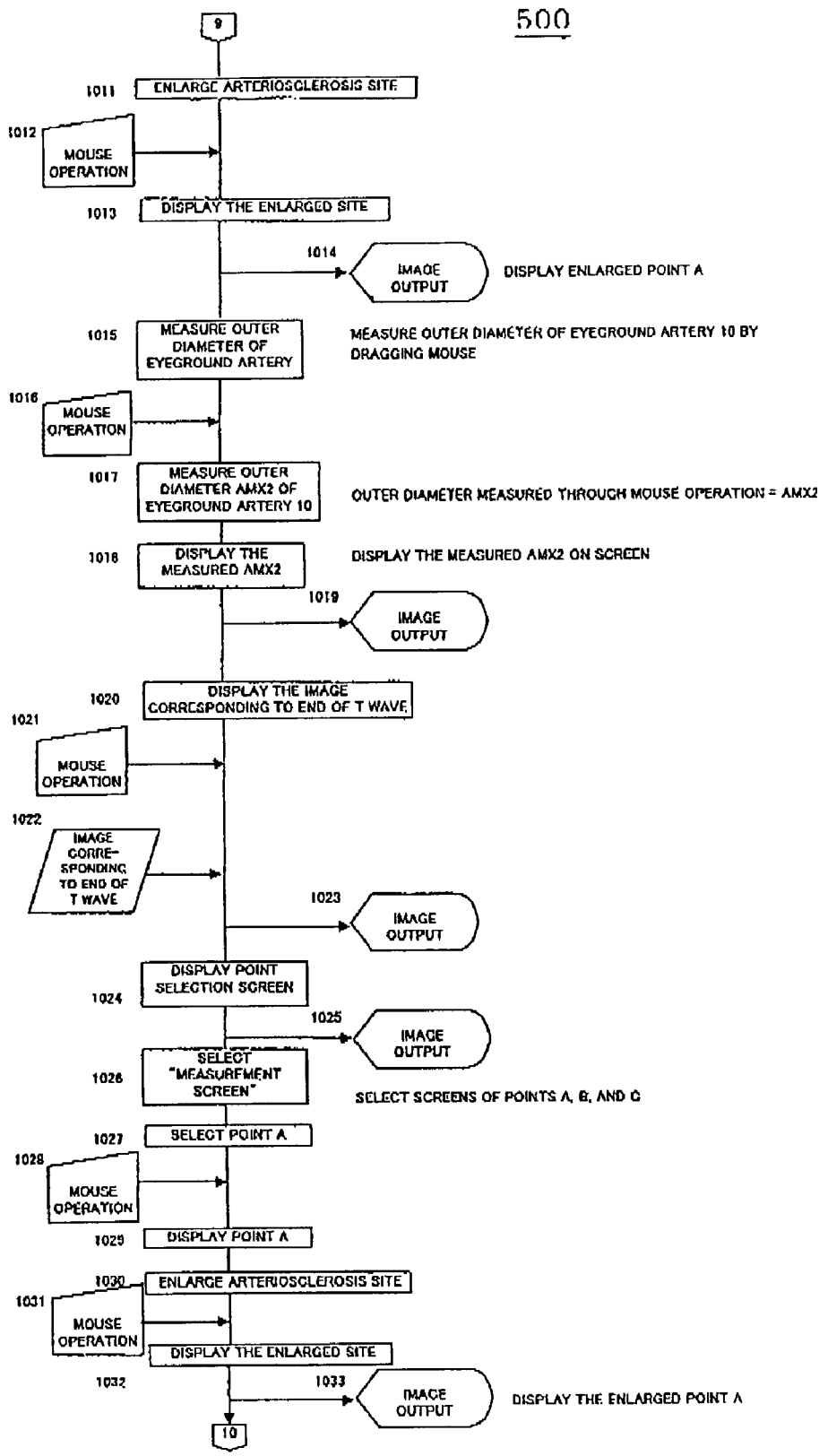
FIG. 6J is the tenth segment of the flowchart illustrating the present software employed in the computer processing apparatus of the present electronic detection system.

Firstly, an eyeground image synchronized with the peak of an R wave of an electrocardiographic signal is displayed (1001). Specifically, data of an eyeground image (photographed at a view angle of 50°) synchronized with the peak of the R wave are output (1003 through 1006) through mouse operation (1002), and a measurement screen is selected (1007). As described above, point A is selected (1008). Specifically, point A is displayed (1010) through mouse operation (1009), and data of an enlarged image of an arteriosclerosis site (photographed at a view angle of 25°) are output (1011 through 1014) (FIG. 6J). Subsequently, the diameter (AMX2) of an eyeground vein 10 at the arteriosclerosis site is measured by dragging a mouse, and image data of the measured diameter are output (1015 through 1019).

Furthermore, an eyeground image synchronized with the end of a T wave of the electrocardiographic signal is displayed (1020). Specifically, data of an eyeground image (photographed at a view angle of 50°) synchronized with the end of the T wave are output (1022 through 1025) through mouse operation (1021), and a measurement screen is selected (1026). In a manner similar to that described above, point A is selected (1027). Specifically, point A is displayed (1029) through mouse operation (1028), and data of an enlarged image of an arteriosclerosis site (photographed at a view angle of 25°) are output (1030 through 1033). Subsequently, the diameter (AMN2) of an eyeground vein 10 at the arteriosclerosis site is measured by dragging a mouse, and image data of the measured diameter are output (1034 through 1038) (FIG. 6K).

Subsequently, the difference (FX ratio) between AMX2 and AMN2 measured in the above process is obtained (1039). The FX ratio is employed as an index of blood vessel flexibility. Finally, the FX ratio and image data of the FX ratio are stored (1040, 1041).

Thus, an embodiment of the process of detecting arteriosclerosis of a subject employing the present electronic detection system 50 is ended (1042).

Data Confirmation/Display Process

Next will be described a data confirmation process (2000) in the case where "display" is selected from the initial menu of the flowchart at the selection step (0004).

Figure 6L:
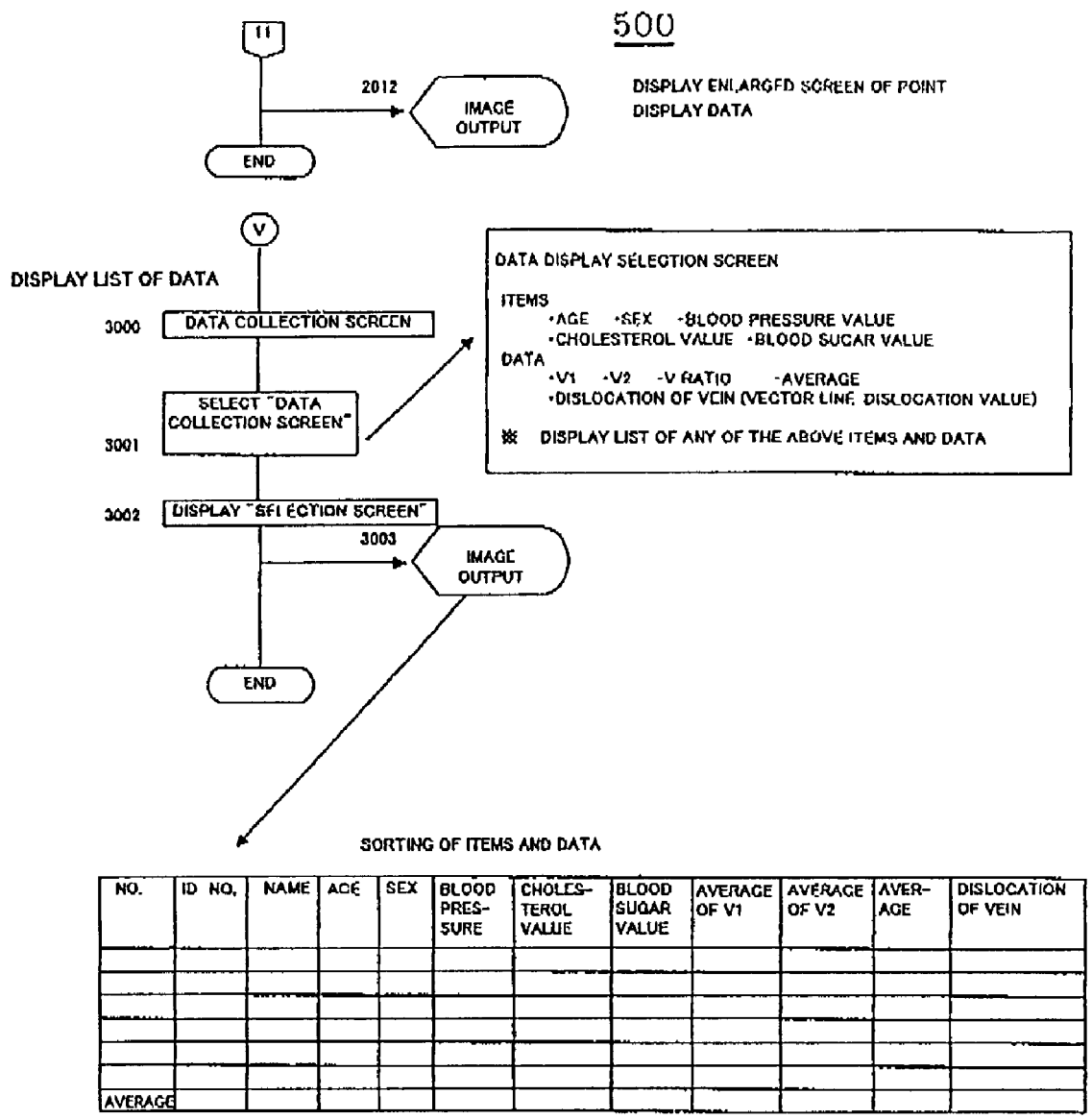
FIG. 6L is the twelfth segment of the flowchart illustrating the present software employed in the computer processing apparatus of the present electronic detection system.

When "display" is selected from the initial menu at the selection step (0004) so as to perform process (IV), a keyboard input screen is displayed (2001). When the ID No. of a subject is input by use of a keyboard (2002), image data of the subject are output (2003). After the data of the subject are confirmed, a data judgment step is performed (2004). In the case where errors are recognized in the data of the subject in a judgemnt step (2005) and the data must be modified (i.e., in the case of NO), the data are modified on the keyboard input screen by use of a keyboard, and the above process is repeated (repeating process (a)). In contrast, in the case where no modification of the data of the subject is required (i.e., in the case of YES), image data of points A, B, and C are output (2006, 2007), and each of the points is displayed on the screen. A desired point is selected from these points on the screen and clicked (2008, 2009), image data of an enlarged screen of the selected point are output (2011) through mouse operation (2010), and the enlarged screen and the data are displayed (2012) (FIG. 6L). Thus, the data confirmation/display process is ended.

Data List Display Process

Next will be described a data list display process (3000) performed in the case where "collection" is selected from the initial menu of the flowchart at the selection step (0004).

When "collection" is selected from the initial menu at the selection step (0004) so as to perform process (V) (3001), a data display screen is displayed, and a menu of data collection formats is displayed. When a desired collection format is selected from the collection menu (3002), image data of display of a list of items are output (3003). After the list of data is displayed, the data list display process is ended.

What is claimed is:

1. An arteriosclerosis detection system comprising:
   electrocardiographic signal detection means for detecting an electrocardiographic signal;
   eyeground image detection means for continuously or discontinuously detecting an eyeground image in synchronization with the detected electrocardiographic signal; and
   eyeground vein constriction detection means for detecting constriction of an eyeground vein by using a ratio of an outer diameter of the eyeground vein in a vicinity of a site at which the eyeground vein and an eyeground artery cross each other to a portion of the eyeground vein distant from the crossing site,
   wherein the system is operable to detect the constriction on the basis of the eyeground image detected in synchronization with the electrocardiographic signal.

2. The arteriosclerosis detection system according to claim 1, wherein the electrocardiographic signal comprises at least one of an electrocardiographic R wave and T wave.

3. The arteriosclerosis detection system according to claim 1, wherein arteriosclerosis is detected by employment, as an arteriosclerosis index, of a degree of the constriction of an eye ground vein in a vicinity of a crossing site of an eyeground artery and the eyeground vein, the constriction degree being obtained using the eyeground image detection means.

4. The arteriosclerosis detection system according to claim 1, wherein the system is operable to detect a degree of aging of an artery of the subject by correlating normalized data obtained by normalizing, in accordance with the ages of a plurality of subjects, a degree of the constriction of an eyeground vein in a vicinity of a crossing site of an eyeground artery and the eyeground vein, the constriction degree being obtained using the arteriosclerosis detection system, with the degree of the constriction of each of the subjects.

5. An arteriosclerosis detection system comprising:
   electrocardiographic signal detection means for detecting an electrocardiographic signal;
   eyeground image detection means for continuously or discontinuously detecting an eyeground image in synchronization with an electrocardiographic signal detected by the detection means; and
   eyeground vein constriction detection means for detecting the constriction of an eyeground vein by using a ratio of an outer diameter of the eyeground vein in the vicinity of a site at which the eyeground vein and an eyeground artery cross each other to a portion of a eyeground vein distant from the crossing site,
   wherein the system is operable to detect the constriction of the eyeground vein based on the eyeground image detected in synchronization with the electrocardiographic signal, and
   wherein the system is operable to detect the eyeground image using software which can provide an eyeground image synchronized with an electrocardiographic signal by obtaining, by use of a computer, a stationary eyeground image synchronized with an arbitrary electrocardiographic signal from an animated eyeground image.

6. The arteriosclerosis detection system according to claim 5, wherein the software is configured to extract an eyeground image that is synchronized with an arbitrary electrocardiographic signal while displaying animated images of the eyeground and electrocardiogram on display means of a computer terminal.

7. The arteriosclerosis detection system according to claim 5, wherein the electrocardiographic signal comprises at least one of an electrocardiographic R wave and T wave.

8. The arteriosclerosis detection system according to claim 5, wherein the software is configured to detect arteriosclerosis using means for calculating a degree of the constriction of the eyeground vein in a vicinity of a crossing site of an eyeground artery and the eyeground vein, and for correlating, the calculated value obtained through the calculation with the degree of arteriosclerosis.

9. The arteriosclerosis detection system according to claim 8, wherein the calculated value is a consolidated value of calculation values obtained for different electrocardiographic signals.

10. The arteriosclerosis detection system according to claim 8, wherein the calculated value is a consolidated value of calculation values obtained from eyeground images of two or more portions, each portion corresponding to a crossing site or its vicinity of an eyeground artery and an eyeground vein.

11. The arteriosclerosis detection system according to claim 8, wherein the software is provided with means for calculating the rate of change in calculation values corresponding to different electrocardiographic signals.

12. The arteriosclerosis detection system according to claim 8, wherein the software is provided with means for correlating the rate of change in calculation values and elasticity of the artery for the detection of arteriosclerosis.

13. The arteriosclerosis detection system according to claim 8, further comprising:
a computer-readable medium having an algorithm evaluating the degree of arterial aging of the subject,
wherein the algorithm correlates normalized data obtained by normalizing, in accordance with the ages of a plurality of subjects, calculated values in relation to the degree of constriction of an eyeground vein in the vicinity of the crossing site of the eyeground artery and the eyeground vein, the constriction degree being obtained using the arteriosclerosis detection system, with calculated values in relation to the degree of constriction of each of the subjects.

14. The arteriosclerosis detection system according to claim 1, wherein the ratio is corrected by a correction value obtained from attributes of an intersection of the eyeground vein and the eyeground artery, and wherein based on the constriction of the vein arteriosclerosis is detected.

15. The arteriosclerosis detection system according to claim 5, wherein the ratio is corrected by a correction value obtained from attributes of an intersection of the eyeground vein and the eyeground artery.

16. A method of detecting arteriosclerosis, the method comprising:
detecting an electrocardiographic signal;
continuously or discontinuously detecting an eyeground image in synchronization with the detected electrocardiographic signal; and
detecting constriction of an eyeground vein by using a ratio of an outer diameter of the eyeground vein in a vicinity of a site at which the eyeground vein and an eyeground artery across each other to a portion of the eyeground vein distant from the crossing site,
wherein the constriction being detected on basis of the eyeground image detected in synchronization with the electrocardiographic signal.

* * * * *